US011786292B2

(12) United States Patent
Fox et al.

(10) Patent No.: US 11,786,292 B2
(45) Date of Patent: *Oct. 17, 2023

(54) INTEGRATED NASAL NERVE DETECTOR ABLATION-APPARATUS, NASAL NERVE LOCATOR, AND METHODS OF USE

(71) Applicant: Arrinex, Inc., Redwood City, CA (US)

(72) Inventors: William Jason Fox, San Mateo, CA (US); David Moosavi, Redwood City, CA (US); Mojgan Saadat, Atherton, CA (US); Vahid Saadat, Atherton, CA (US); Caroline Sobek, Redwood City, CA (US); Neekon Saadat, Redwood City, CA (US)

(73) Assignee: Arrinex, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,889

(22) Filed: Jan. 14, 2022

(65) Prior Publication Data
US 2022/0133395 A1    May 5, 2022

Related U.S. Application Data

(63) Continuation of application No. 15/786,306, filed on Oct. 17, 2017, now Pat. No. 11,253,312.
(Continued)

(51) Int. Cl.
*A61B 18/14*    (2006.01)
*A61B 18/02*    (2006.01)
(Continued)

(52) U.S. Cl.
CPC ............ *A61B 18/1442* (2013.01); *A61B 5/01* (2013.01); *A61B 5/0538* (2013.01); *A61B 5/065* (2013.01);
(Continued)

(58) Field of Classification Search
CPC .......... A61B 17/24; A61B 2018/00327; A61B 2018/00577; A61B 2018/0212;
(Continued)

(56) References Cited

U.S. PATENT DOCUMENTS 5,527,351 A    6/1996 Friedman
5,611,796 A    3/1997 Kamami
(Continued)

FOREIGN PATENT DOCUMENTS

EP    2532300    12/2012
EP    2662027    11/2013
(Continued)

OTHER PUBLICATIONS

Anggard, "The Effects of Parasympathetic Nerve Stimulation on the Microcirculation and Secretion in the Nasal Musosa of the Cate", Acta Oto-Laryngologica, pp. 1-9 (2009)*.
(Continued)

*Primary Examiner* — Ronald Hupczey, Jr.
*Assistant Examiner* — Bradford C. Blaise
(74) *Attorney, Agent, or Firm* — McDonnell Boehnen Hulbert & Berghoff LLP

(57) ABSTRACT

Systems and related methods for identifying and/or ablating targeted nerves are provided. A probe with stimulating electrodes and/or ablation members are provided. The probe may be inserted into a nasal cavity and current may be introduced through the electrodes to stimulate a targeted area. The response to stimulation may be used to identify the targeted nerve. Once identified, the ablation member may ablate the targeted nerve.

18 Claims, 15 Drawing Sheets

Related U.S. Application Data

(60) Provisional application No. 62/408,920, filed on Oct. 17, 2016.

(51) Int. Cl.
| | |
|---|---|
| *A61B 5/00* | (2006.01) |
| *A61B 5/06* | (2006.01) |
| *A61B 5/01* | (2006.01) |
| *A61B 5/0538* | (2021.01) |
| *A61B 18/00* | (2006.01) |
| *A61B 17/24* | (2006.01) |
| *A61B 34/20* | (2016.01) |
| *A61N 1/36* | (2006.01) |

(52) U.S. Cl.
CPC .......... *A61B 5/4836* (2013.01); *A61B 5/4893* (2013.01); *A61B 5/6819* (2013.01); *A61B 5/6877* (2013.01); *A61B 18/02* (2013.01); *A61B 18/1492* (2013.01); *A61B 17/24* (2013.01); *A61B 18/1485* (2013.01); *A61B 34/20* (2016.02); *A61B 2018/0022* (2013.01); *A61B 2018/00327* (2013.01); *A61B 2018/00434* (2013.01); *A61B 2018/00577* (2013.01); *A61B 2018/00696* (2013.01); *A61B 2018/00791* (2013.01); *A61B 2018/00875* (2013.01); *A61B 2018/00904* (2013.01); *A61B 2018/00982* (2013.01); *A61B 2018/0212* (2013.01); *A61B 2018/1495* (2013.01); *A61B 2562/0209* (2013.01); *A61N 1/36* (2013.01)

(58) Field of Classification Search
CPC ............ A61B 2018/1467; A61B 18/02; A61B 18/1482; A61B 18/1485; A61B 18/1492; A61B 18/1495
See application file for complete search history.

(56) References Cited

U.S. PATENT DOCUMENTS

| | | | |
|---|---|---|---|
| 5,733,280 | A | 3/1998 | Avitall |
| 5,899,898 | A | 5/1999 | Arless |
| 5,899,899 | A | 5/1999 | Arless |
| 5,971,979 | A | 10/1999 | Joye |
| 6,045,549 | A | 4/2000 | Smethers |
| 6,106,518 | A | 8/2000 | Wittenberger |
| 6,210,355 | B1 | 4/2001 | Edwards |
| 6,270,476 | B1 | 8/2001 | Santoianni |
| 6,283,959 | B1 | 9/2001 | Lalonde |
| 6,355,029 | B1 | 3/2002 | Joye |
| 6,375,654 | B1 | 4/2002 | McIntyre |
| 6,428,534 | B1 | 8/2002 | Joye |
| 6,432,102 | B2 | 8/2002 | Joye |
| 6,514,245 | B1 | 2/2003 | Williams |
| 6,517,533 | B1 | 2/2003 | Swaminathan |
| 6,537,271 | B1 | 3/2003 | Murray |
| 6,575,966 | B2 | 6/2003 | Lane |
| 6,595,988 | B2 | 7/2003 | Wittenberger |
| 6,602,276 | B2 | 8/2003 | Dobak, III |
| 6,648,879 | B2 | 11/2003 | Joye |
| 6,666,858 | B2 | 12/2003 | Lafontaine |
| 6,673,066 | B2 | 1/2004 | Wemeth |
| 6,685,732 | B2 | 2/2004 | Kramer |
| 6,736,809 | B2 | 5/2004 | Capuano |
| 6,786,900 | B2 | 9/2004 | Joye |
| 6,786,901 | B2 | 9/2004 | Joye |
| 6,811,550 | B2 | 11/2004 | Holland |
| 6,875,209 | B2 | 4/2005 | Zvuloni |
| 6,905,494 | B2 | 6/2005 | Von |
| 6,908,462 | B2 | 6/2005 | Joye |
| 6,949,096 | B2 | 9/2005 | Davison |
| 6,972,015 | B2 | 12/2005 | Joye |
| 6,989,009 | B2 | 1/2006 | Lafontaine |
| 6,991,631 | B2 | 1/2006 | Woloszko |
| 7,001,378 | B2 | 2/2006 | Yon |
| 7,060,062 | B2 | 6/2006 | Joye |
| 7,081,112 | B2 | 7/2006 | Joye |
| 7,101,368 | B2 | 9/2006 | Lafontaine |
| 7,104,984 | B2 | 9/2006 | Ryba |
| 7,189,227 | B2 | 3/2007 | Lafontaine |
| 7,288,089 | B2 | 10/2007 | Von |
| 7,291,144 | B2 | 11/2007 | Dobak, III |
| 7,300,433 | B2 | 11/2007 | Lane |
| 7,354,434 | B2 | 4/2008 | Zvuloni |
| 7,418,292 | B2 | 8/2008 | Shafer |
| 7,442,190 | B2 | 10/2008 | Abboud |
| 7,449,018 | B2 | 11/2008 | Kramer |
| 7,527,622 | B2 | 5/2009 | Lane |
| 7,641,679 | B2 | 1/2010 | Joye |
| 7,648,497 | B2 | 1/2010 | Lane |
| 7,727,191 | B2 | 6/2010 | Mihalik |
| 7,727,228 | B2 | 6/2010 | Abboud |
| 7,740,627 | B2 | 6/2010 | Gammie |
| 7,769,442 | B2 | 8/2010 | Shafer |
| 7,794,455 | B2 | 9/2010 | Abboud |
| 7,842,031 | B2 | 11/2010 | Abboud |
| 7,862,557 | B2 | 1/2011 | Joye |
| 7,892,230 | B2 | 2/2011 | Woloszko |
| 8,043,283 | B2 | 10/2011 | Dobak, III |
| 8,043,351 | B2 | 10/2011 | Yon |
| 8,088,127 | B2 | 1/2012 | Mayse |
| 8,142,424 | B2 | 3/2012 | Swanson |
| 8,157,794 | B2 | 4/2012 | Dobak, III |
| 8,177,779 | B2 | 5/2012 | Joye |
| 8,187,261 | B2 | 5/2012 | Watson |
| 8,231,613 | B2 | 7/2012 | Baxter |
| 8,235,976 | B2 | 8/2012 | Lafontaine |
| 8,292,887 | B2 | 10/2012 | Woloszko |
| 8,298,217 | B2 | 10/2012 | Lane |
| 8,333,758 | B2 | 12/2012 | Joye |
| 8,382,746 | B2 | 2/2013 | Williams |
| 8,382,747 | B2 | 2/2013 | Abboud |
| 8,388,600 | B1 | 3/2013 | Eldredge |
| 8,394,075 | B2 | 3/2013 | Ansarinia |
| 8,425,456 | B2 | 4/2013 | Mihalik |
| 8,425,457 | B2 | 4/2013 | John |
| 8,439,906 | B2 | 5/2013 | Watson |
| 8,465,481 | B2 | 6/2013 | Mazzone |
| 8,475,440 | B2 | 7/2013 | Abboud |
| 8,480,664 | B2 | 7/2013 | Watson |
| 8,491,636 | B2 | 7/2013 | Abboud |
| 8,512,324 | B2 | 8/2013 | Abboud |
| 8,545,491 | B2 | 10/2013 | Abboud |
| 8,591,504 | B2 | 11/2013 | Tin |
| 8,617,149 | B2 | 12/2013 | Lafontaine |
| 8,632,529 | B2 | 1/2014 | Bencini |
| 8,663,211 | B2 | 3/2014 | Fourkas |
| 8,672,930 | B2 | 3/2014 | Wittenberger |
| 8,676,324 | B2 | 3/2014 | Simon |
| 8,679,104 | B2 | 3/2014 | Abboud |
| 8,679,105 | B2 | 3/2014 | Wittenberger |
| 8,715,274 | B2 | 5/2014 | Watson |
| 8,715,275 | B2 | 5/2014 | Burger |
| 8,747,401 | B2 | 6/2014 | Gonzalez |
| 8,764,740 | B2 | 7/2014 | Watson |
| 8,771,264 | B2 | 7/2014 | Abboud |
| 8,827,952 | B2 | 9/2014 | Subramaniam |
| 8,900,222 | B2 | 12/2014 | Abboud |
| 8,911,434 | B2 | 12/2014 | Wittenberger |
| 8,926,602 | B2 | 1/2015 | Pageard |
| 8,936,594 | B2 | 1/2015 | Wolf |
| 8,945,107 | B2 | 2/2015 | Buckley |
| 8,986,293 | B2 | 3/2015 | Desrochers |
| 8,986,301 | B2 | 3/2015 | Wolf |
| 8,996,137 | B2 | 3/2015 | Ackermann |
| 9,050,073 | B2 | 6/2015 | Newell |
| 9,050,074 | B2 | 6/2015 | Joye |
| 9,060,754 | B2 | 6/2015 | Buckley |
| 9,060,755 | B2 | 6/2015 | Buckley |
| 9,066,713 | B2 | 6/2015 | Turovskiy |
| 9,072,597 | B2 | 7/2015 | Wolf |
| 9,084,590 | B2 | 7/2015 | Wittenberger |

(56) References Cited

U.S. PATENT DOCUMENTS

| | | |
|---|---|---|
| 9,084,592 B2 | 7/2015 | Wu |
| 9,089,314 B2 | 7/2015 | Wittenberger |
| 9,101,346 B2 | 8/2015 | Burger |
| 9,168,079 B2 | 10/2015 | Lalonde |
| 9,168,081 B2 | 10/2015 | Williams |
| 9,179,964 B2 | 11/2015 | Wolf |
| 9,179,967 B2 | 11/2015 | Wolf |
| 9,211,393 B2 | 12/2015 | Hu |
| 9,220,556 B2 | 12/2015 | Lalonde |
| 9,237,924 B2 | 1/2016 | Wolf |
| 9,241,752 B2 | 1/2016 | Nash |
| 9,254,166 B2 | 2/2016 | Aluru |
| 9,265,956 B2 | 2/2016 | Ackermann |
| 9,333,023 B2 | 5/2016 | Wittenberger |
| 9,414,878 B1 | 8/2016 | Wu |
| 9,415,194 B2 | 8/2016 | Wolf |
| 9,433,463 B2 | 9/2016 | Wolf |
| 9,439,709 B2 | 9/2016 | Duong |
| 9,445,859 B2 | 9/2016 | Pageard |
| 9,452,010 B2 | 9/2016 | Wolf |
| 9,480,521 B2 | 11/2016 | Kim |
| 9,486,278 B2 | 11/2016 | Wolf |
| 9,522,030 B2 | 12/2016 | Harmouche |
| 9,526,571 B2 | 12/2016 | Wolf |
| 9,555,223 B2 | 1/2017 | Abboud |
| 9,572,536 B2 | 2/2017 | Abboud |
| 9,801,752 B2 | 10/2017 | Wolf |
| 11,253,312 B2 * | 2/2022 | Fox .............. A61B 5/065 |
| 2003/0144659 A1 | 7/2003 | Edwards |
| 2004/0015068 A1 * | 1/2004 | Shalev ........... A61N 1/0546 600/378 |
| 2004/0024412 A1 | 2/2004 | Clements |
| 2006/0235474 A1 | 10/2006 | Demarais |
| 2006/0276852 A1 | 12/2006 | Demarais |
| 2007/0173899 A1 | 7/2007 | Levin |
| 2007/0265687 A1 | 11/2007 | Deem |
| 2007/0299433 A1 | 12/2007 | Williams |
| 2008/0009851 A1 | 1/2008 | Wittenberger |
| 2008/0009925 A1 | 1/2008 | Abboud |
| 2008/0027423 A1 | 1/2008 | Choi |
| 2008/0119693 A1 | 5/2008 | Makower |
| 2009/0036948 A1 | 2/2009 | Levin |
| 2009/0062873 A1 | 3/2009 | Wu |
| 2009/0076409 A1 | 3/2009 | Wu |
| 2009/0182318 A1 | 7/2009 | Abboud |
| 2009/0234345 A1 | 9/2009 | Hon |
| 2010/0057150 A1 | 3/2010 | Demarais |
| 2010/0137860 A1 | 6/2010 | Demarais |
| 2010/0137952 A1 | 6/2010 | Demarais |
| 2010/0168731 A1 | 7/2010 | Wu |
| 2010/0168739 A1 | 7/2010 | Wu |
| 2010/0174282 A1 | 7/2010 | Demarais |
| 2010/0191112 A1 | 7/2010 | Demarais |
| 2011/0152855 A1 | 6/2011 | Mayse |
| 2011/0184402 A1 | 7/2011 | Baust |
| 2012/0029493 A1 | 2/2012 | Wittenberger |
| 2012/0191003 A1 | 7/2012 | Garabedian |
| 2013/0006326 A1 | 1/2013 | Ackermann |
| 2013/0018366 A1 | 1/2013 | Wu |
| 2013/0218151 A1 | 8/2013 | Mihalik |
| 2013/0253387 A1 | 9/2013 | Bonutti |
| 2013/0310822 A1 | 11/2013 | Mayse |
| 2013/0345699 A1 | 12/2013 | Brannan |
| 2013/0345700 A1 | 12/2013 | Hlavka |
| 2014/0058369 A1 | 2/2014 | Hon |
| 2014/0186341 A1 | 7/2014 | Mayse |
| 2014/0207130 A1 | 7/2014 | Fourkas |
| 2014/0229975 A1 | 8/2014 | Bolden |
| 2014/0236148 A1 | 8/2014 | Hlavka |
| 2014/0257271 A1 | 9/2014 | Mayse |
| 2014/0276792 A1 | 9/2014 | Kaveckis |
| 2014/0277429 A1 | 9/2014 | Kuzma |
| 2014/0316310 A1 | 10/2014 | Ackermann |
| 2014/0371812 A1 | 12/2014 | Ackermann |
| 2015/0011843 A1 | 1/2015 | Toth |
| 2015/0031946 A1 | 1/2015 | Saadat |
| 2015/0045781 A1 | 2/2015 | Abboud |
| 2015/0080870 A1 | 3/2015 | Wittenberger |
| 2015/0119868 A1 | 4/2015 | Lalonde |
| 2015/0126986 A1 | 5/2015 | Kelly |
| 2015/0157382 A1 | 6/2015 | Avitall |
| 2015/0164401 A1 | 6/2015 | Toth |
| 2015/0164571 A1 | 6/2015 | Saadat |
| 2015/0196345 A1 | 6/2015 | Newell |
| 2015/0190188 A1 | 7/2015 | Lalonde |
| 2015/0196740 A1 | 7/2015 | Mallin |
| 2015/0223860 A1 | 8/2015 | Wittenberger |
| 2015/0238754 A1 | 8/2015 | Loudin |
| 2015/0250524 A1 | 9/2015 | Moriarty |
| 2015/0265329 A1 | 9/2015 | Lalonde |
| 2015/0265812 A1 | 9/2015 | Lalonde |
| 2015/0297846 A1 | 10/2015 | Given |
| 2015/0313661 A1 | 11/2015 | Wu |
| 2016/0022992 A1 | 1/2016 | Franke |
| 2016/0038212 A1 | 2/2016 | Rybe |
| 2016/0045277 A1 | 2/2016 | Lin |
| 2016/0066975 A1 | 3/2016 | Fourkas |
| 2016/0074090 A1 | 3/2016 | Lalonde |
| 2016/0114163 A1 | 4/2016 | Franke |
| 2016/0114172 A1 | 4/2016 | Loudin |
| 2016/0012118 A1 | 5/2016 | Sirer |
| 2016/0143683 A1 | 5/2016 | Aluru |
| 2016/0158548 A1 | 6/2016 | Ackermann |
| 2016/0166305 A1 | 6/2016 | Nash |
| 2016/0166306 A1 | 6/2016 | Pageard |
| 2016/0220295 A1 | 8/2016 | Wittenberger |
| 2016/0287315 A1 | 10/2016 | Wolf |
| 2016/0317794 A1 | 11/2016 | Saadat |
| 2016/0331433 A1 | 11/2016 | Wu |
| 2016/0331459 A1 | 11/2016 | Townley |
| 2016/0354134 A1 | 12/2016 | Pageard |
| 2016/0354135 A1 | 12/2016 | Saadat |
| 2016/0354136 A1 | 12/2016 | Saadat |
| 2016/0361112 A1 | 12/2016 | Wolf |
| 2017/0007316 A1 | 1/2017 | Wolf |
| 2017/0014258 A1 | 1/2017 | Wolf |
| 2017/0042601 A1 | 2/2017 | Kim |
| 2017/0056087 A1 | 3/2017 | Buckley |
| 2017/0056632 A1 | 3/2017 | Jenkins |
| 2017/0231474 A1 | 8/2017 | Saadat |
| 2017/0360494 A1 | 12/2017 | Saadat |
| 2018/0078327 A1 | 3/2018 | Lin |

FOREIGN PATENT DOCUMENTS

| | | |
|---|---|---|
| EP | 2662046 | 11/2013 |
| EP | 2662116 | 11/2013 |
| WO | 9902018 | 4/1999 |
| WO | 9927862 | 6/1999 |
| WO | 1999030655 | 6/1999 |
| WO | 2000009053 | 2/2000 |
| WO | 0047118 | 8/2000 |
| WO | 0054684 | 9/2000 |
| WO | 0164145 | 9/2001 |
| WO | 0195819 | 12/2001 |
| WO | 0204042 | 1/2002 |
| WO | 0207628 | 4/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2005108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |
| WO | 2007145759 | 12/2007 |

(56) References Cited

FOREIGN PATENT DOCUMENTS

| | | |
|---|---|---|
| WO | 2008000065 | 1/2008 |
| WO | 2008042890 | 4/2008 |
| WO | 2008046183 | 4/2008 |
| WO | 2008051918 | 5/2008 |
| WO | 2008157042 | 12/2008 |
| WO | 2009114701 | 9/2009 |
| WO | 2009146372 | 12/2009 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |
| WO | 2012012868 | 2/2012 |
| WO | 2012012869 | 2/2012 |
| WO | 2012015636 | 2/2012 |
| WO | 2012019156 | 2/2012 |
| WO | 2012051697 | 4/2012 |
| WO | 2012027647 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 2012174161 | 12/2012 |
| WO | 2013035192 | 3/2013 |
| WO | 2013110156 | 8/2013 |
| WO | 2013163325 | 2/2014 |
| WO | 2014113864 | 7/2014 |
| WO | 2014138867 | 9/2014 |
| WO | 2015038523 | 3/2015 |
| WO | 2015048806 | 4/2015 |
| WO | 2015061883 | 5/2015 |
| WO | 201508142 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |
| WO | 2014138866 | 9/2018 |

OTHER PUBLICATIONS

Arora et al. "Cryodestruction of Vidian Nerve Branches", Indian Journal of Otolaryngology, 32(3):80-80 (1980)*.
Bicknell et al., "Cryosurgery for Allergic and Vasomotor Rhinitis", The Journal of Laryngology and Otology, 93:143-146 (1979)*.
Bluestone et al., "Intranasal Freezing for Severe Epistaxis", Arch Otolaryng., 85:119-121 (1967)*.
Bumsted "Cryotherapy for Chronic Vasomotor Rhinitis: Technique and Patient Selection for Improved Results", Laryngoscope, 94:539-544 (1984)*.
Costa et al., "Radiographic and Anatomic Characterization of the Nasal Septal Swell Body", Arch Otolaryngol Head Neck Surg., 136(11):1109 (2010)*.
Girdhar-Gopal, "An Assessment of Postganglionic Cryoneurolysis for Managing Vasomotor Rhinitis", American Journal of Rhinology, 8(4):157-164 (1994)*.
Golhar et al., "The effect of Cryodestruction of Vidian Nasal Branches on Nasal Mucus Flow in Vasomotor Rhinitis", Indian Journal of Otolaryngology, 33(1):12-14 (1981)*.
Goode, "A Liquid Nitrogen Turbinate Probe for Hypertrophic Rhinitis", Arch Otolaryngol., 103:431 (1977).
Gurelik et al. "The Effects of the Electrical Stimulation of the Nasal Mucosa on Cortical Cerebral Blood Flow in Rabbits", Neuroscience Letters, 365:210-213 (2004)*.
Mehra et al., "Cryosurgery in Vasomotor Rhinitis—An Analysis of 156 Patients", Indian Journal of Otolaryngology, 42(3):95-98 (1990)*.
Ozenberger, "Cryosurgery for the Treatment of Chronic Rhinitis", Laryngoscope, 83(4):508-516 (1973)*.
Ozenberger, "Cryosurgery in Chronic Rhinitis", Laryngoscope, 80(5):723-734 (1970)*.
Principato, "Chronic Vasomotor Rhinitis: Cryogenic and other Surgical Mode of Treatment", The Laryngoscope, 89:619-638 (1979)*.
Rao, "Cryosurgery on inferior turbinate hypertrophy under topical anaesthesia—is it boon in electricity deprived places", National Journal of Otohinolaryngology and Head & Neck Surgery, 1(10):7-9 (2013)*.
Sanu, "Two Hundred Years of Controversty Between UK and USA", Rhinology, 86-91*.
Schwartz, "Autonomix Neurophysiologic Sensing Technology", Autonomix Medical, Inc. Paper, Aug. 1, 2016, 4 pages*.
Settipane et al., "Update on Nonallergic Rhinitis", Annals of Allergy Asthma & Immunology, 86:494-508 (2001)*.
Strome, A long-term assessment of cryotherapy for treating vasomotor instability, 69(12):839-842 (1990)*.
Tero et al., "Cryosurgery on Postgaglionic Fibers (Posterior Nasal Branches) of the Pterygopalatine Ganglion for Vasomotor Rhinitis", Acta Otolaryngol. 96:139-148 (1983)*.

* cited by examiner

| Electrical Parameter | Details |
|---|---|
| Discharge rate of autonomic fibers | 1-2 imp/sec |
| Impulse Rate | Nasal secretions and increased arterial blood flow frequency-dependent between 0.5-12 imp/sec, minimum effective frequency between 2-5 imp/sec, maximum secretion at 15 imp/sec |
| Frequency | Minimum frequency between 2 and 5 hertz, maximum frequency of 10 to 15 hertz<br><br>1-250 Hz<br><br>10 Hz<br><br>14 Hz<br><br>0.5-250 Hz<br><br>20 Hz<br><br>5-150 Hz<br><br>6.6-30 Hz |
| Pulse Width | 1 msec<br><br>10-1000 microseconds (TENS device)<br><br>5 msec<br><br>210 microseconds<br><br>10-1500 microseconds<br><br>0.2 msec<br><br>0.05-1.5 msec<br><br>0.02-0.05 msec |
| Intensity | 8V<br><br>9V (TENS device, from batteries)<br><br>0.5-8V<br><br>0.1-5V |

FIG. 17

INTEGRATED NASAL NERVE DETECTOR ABLATION-APPARATUS, NASAL NERVE LOCATOR, AND METHODS OF USE

CROSS REFERENCE TO RELATED APPLICATIONS

This application is a continuation of U.S. patent application Ser. No. 15/786,306, filed Oct. 17, 2017, now issued U.S. Pat. No. 11,253,312, which claims the priority to U.S. Provisional Application No. 62/408,920 filed on Oct. 17, 2016, the contents of each of which are incorporated by reference herein in their entirety for all purposes.

BACKGROUND

The major symptoms of allergic or non-allergic chronic rhinitis are sneezing, rhinorrhea, and night time coughing which are brought about by mucosal swelling, hyper-responsiveness of the sensory nerves, and an increased number and augmented responses of secretory cells in the inferior turbinates, respectively. In particular, chronic severe nasal obstruction resulting from remodeling of submucosal tissues of the inferior turbinates due to dilation of the venous sinuses or fibrosis can interfere with the quality of life.

One strategy is the surgical treatment of chronic rhinitis; that is to physically eliminate the tissue of the inferior turbinate. Removal or ablation of the mucosal tissue including the surface epithelial layer has the disadvantage of postoperative complications such as crusting and an increased infection rate. Cauterization of the surface epithelia of the inferior turbinate using electrocautery, cryosurgery, or laser yields only short-term benefits to nasal breathing. Submucosal diathermy or cryosurgery also shows only a short-term effect. Turbinectomy is thought to have the greatest effect on nasal obstruction, and slight improvement in some rhinitis patients but it is accompanied by severe adverse effects such as bleeding, crusting, and nasal dryness.

Golding-Wood, who recommended cutting the parasympathetic nerve fibers in the vidian canal to decrease the parasympathetic tone to the nasal mucosa, introduced a different approach for the treatment of hypersecretion in 1961. Various approaches to the vidian canal were subsequently developed, and the method was widely employed in the 1970s. However, the original technique was abandoned at the beginning of the 1980s because of its irreversible complications such as dry eyes.

The pterygoid canal carries both parasympathetic and sympathetic fibers, namely the vidian nerve, to the sphenopalatine ganglion. Subsequently, these autonomic fibers, which relay in the sphenopalatine ganglion, reach the nasal mucosa through the sphenopalatine foramen as the posterior nasal nerves. The posterior nasal nerve, which follows the sphenopalatine artery and vein, arises within the sphenopalatine foramen. Similar to vidian neurectomy, selective interruption of the posterior nasal nerves, which interrupts the somatic afferent innervation to the nasal mucosa, can be expected to reduce the hypersensitivity and axon reflexes of the nasal mucosa, however it has no complications, like those of vidian neurectomy, since the secretomotor supply to the lacrimal gland and the somatosensory supply to the palate are intact, and overpenetration of the pterygoid canal does not occur.

Posterior nasal neurectomy, initially developed by Kikawada in 1998 and later modified by Kawamura and Kubo, is a novel alternative method in which neural bundles are selectively cut or cauterized from the sphenopalatine foramen. Autonomic and sensory nerve fibers that pass through the foramen anatomically branch into the inferior turbinate and are distributed around the mucosal layer. Therefore, selective neurectomy at this point enables physicians to theoretically avoid surgical complications such as inhibition of lacrimal secretion.

There are three nerve bundles innervating the superior, middle and inferior turbinates. The posterior, superior lateral nasal branches off of the maxillary nerve (v2) innervate the middle and superior turbinates. A branch of the greater palatine nerve innervates the inferior turbinate. Ablating these nerves leads to a decrease in or interruption of parasympathetic nerve signals that contribute to rhinorrhea in patients with allergic or vasomotor rhinitis.

Ablation (such as but not limited to cryoablation) allows for the ablation of the posterior nasal nerves through overlying mucosa in a non-invasive procedure. However, there is no current method of identifying the location of the nasal nerves during the ablation procedure other than through identifying anatomic landmarks. As a result, these nerves may not be optimally targeted. One obstacle hindering this identification is the fact that these nerve fibers are 2-3 millimeters beneath the mucosal surface. Possible strategies to identify the nerve include taking advantage of the optical, sonic, and visual properties of nervous tissue, identifying the sphenopalatine artery with which the posterior nasal nerves fibers travel, or developing a method to identify the sphenopalatine ganglion, as it is covered with a distinctive bony lamina and is in the general vicinity of the posterior nasal nerves. The present invention takes advantage of these differences to identify the posterior nasal nerves.

Electrical stimulation of parasympathetic nasal nerves causes an increased frequency-dependent rate of flow of nasal secretions and arterial blood flow, as described by Anggard in his experiments with cats. In these experiments, Anggard delivered monophasic, square wave pulses with an intensity of 8 V and a duration of 1 msec to the distal end of the vidian nerve to 12 anesthetized cats, tracking vasodilation by measuring changes in gross pulse rate and tracking nasal secretion through collection in a well, ultimately finding that varying stimulation frequencies affected the nature of the nasal secretion. Between 0.5 and 1.0 imp/sec, the stimulation resulted in a slight watery secretion. Anywhere above 2.5 imp/sec resulted in a rich secretion that sometimes overflowed in the nasal cavity. The disappearance rate of the nasal secretions and blood content also underwent an increase in rate as frequency increased, suggesting that the electrical stimulation of the parasympathetic nerves simultaneously activated both the vascular and secretory responses. However, when the cats were given atropine, an autonomic nerve system blocker, only the secretory response was blocked and the vascular response remained unaffected. This phenomenon shows that while the postganglionic parasympathetic mediator of nasal secretion is cholinergic, the mechanism that causes the vascular response in the nose is different and resistant to atropine and indomethacin.

The methods of this specific study improve upon the methods of past experiments (Tschalussow, 1913; Blier, 1930; Malcomson, 1959; Malm, 1973, Drettner, 1963) studying the vasodilatory response of nasal mucosa because the technique involving the $^{131}$I- labelled serum albumin avoids the previous source of error of nasal secretion affecting varying measurements of the changes in the lumen of nasal passages and the chronic sympathetic denervation that had been performed on the cats isolated the parasympathetic nervous responses by preventing activation of sympathetic vasomotor fibers present in the vidian nerve. U.S. Pat. No. 6,526,318 to Ansarinia and related PCT Publication WO 01/97905 to Ansarinia, which are incorporated herein by reference, describe a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site.

U.S. Pat. No. 6,788,975 to Whitehurst et al., which is incorporated herein by reference, describes an implantable stimulator with at least two electrodes that is small enough to have the electrodes located adjacent to a nerve structure at least partially responsible for epileptic seizures. The nerve structure may include a trigeminal ganglion or ganglia, a trigeminal nerve, or a branch of a trigeminal nerve, a greater occipital nerve, lesser occipital nerve, third occipital nerve, facial nerve, glossopharyngeal nerve, or a branch of any of these neural structures. Electrical stimulation of such targets may provide significant therapeutic benefit in the management of epilepsy.

BRIEF SUMMARY

Some embodiments of the present invention relate to methods and devices for identifying and/or ablating targeted nerves. While the present invention can be useful for a wide variety of nerves and conditions associated therewith, some embodiments of the invention are particularly useful for identifying and ablating nasal nerves to treat rhinitis as described in more detail below. In many embodiments a probe with stimulating electrodes and a cryogenic ablation member are provided. The probe may be inserted into a nasal cavity and current may be introduced through the electrodes to stimulate a targeted area. Since a targeted nerve such as a posterior nasal nerve may respond to such stimulation with increased nasal secretion or blood flow, the response to stimulation may be used to identify the targeted nerve. Once identified, the cryogenic ablation member may ablate the targeted nerve to treat rhinitis.

Thus, in one aspect, a method is provided for identifying and ablating a targeted nasal nerve to induce secretory or vascular changes in nasal tissue innervated by the targeted nerve. The method includes inserting a probe into a nasal cavity, the probe having a probe shaft with at least one stimulating electrode and an ablation member disposed at a distal end of the probe shaft. The method further includes positioning the distal end of the probe shaft so that the at least one stimulating electrode is placed in contact with a nasal tissue region, and introducing an electrical current through the electrode via an electrical source probe so as to stimulate at least one nasal nerve underlying the nasal tissue region in contact with the at least one stimulating electrode.

The method further includes identifying at least one target nasal nerve and ablating the at least one identified target nasal nerve with the ablation member to induce secretory or vascular changes in tissue innervated by the at least one target nasal nerve.

In many embodiments of the method the target nasal nerve may be identified by observing or measuring a response to the stimulation applied. For example, the target nasal nerve may be identified by observing a physiologic response to the electrical current. The physiologic response may an increased nasal secretion and/or an increased arterial blood flow within the nasal cavity. The target nasal nerve may be identified by measuring at least one of a resistance, a temperature, and/or a degree of tumescence in the nasal cavity. For example, if a certain change in resistance or temperature is measured in response to the stimulation applied, the target nasal nerve may be identified thereby. In some embodiments, a visual, audio or haptic feedback may be provided indicating identification of the target nasal nerve.

In many embodiments of the method, the ablation member includes an expandable structure which can aid in positioning the electrodes or the ablation member. The pair of electrodes may be disposed on a surface of the expandable structure and positioning the probe includes expanding the expandable structure so that the stimulating electrodes are placed in contact with the desired region of nasal tissue. As another example, positioning the probe includes expanding the expandable structure to displace overlying mucosal tissue from a desired tissue region. In some embodiments of the method, ablating the identified targeted nasal nerve includes expanding the expandable structure so that the ablation member is in contact with the nasal tissue region overlying the identified target nasal nerve.

In many embodiments of the method, particular regions and/or nerves may be desired to be targeted. In some embodiments, the targeted nasal nerve is a parasympathetic nerve that responds to electrical stimulation with increased secretion or blood flow. For example, the targeted nasal nerve may be a posterior nasal nerve. The nasal tissue region targeted may include a region of a nasal mucosa covering a medial pterygoid plate of a sphenoid bone.

In many embodiments of the method, the electrical current may be optimally controlled so that a desired response is obtained. Characteristics of the electrical current such as the voltage, frequency, pulse rate, and current may be controlled as desired. For example, introducing an electrical current through the electrodes may include delivering electric pulses through the electrodes at a frequency of 0.5 to 12 impulses per second.

In many embodiments of the method, the number and arrangement of the electrodes may be selected to accurately target particular areas. In some embodiments, a pair of electrodes may be used. The pair of electrodes may have a predetermined spacing so as to stimulate a certain depth below a surface in contact with the electrodes. For example, the electrodes may have a predetermined spacing so as to stimulate 1-5 mm under the surface in contact with the stimulating electrodes. As another example, the electrodes may have a predetermined spacing so as to stimulate 1-3 mm under the surface in contact with the stimulating electrodes. The electrodes may also be disposed on a distal tip that is releasably coupled to the probe shaft.

In many embodiments the method further includes confirming that the targeted nasal nerve has been ablated to ensure adequate response. For example, the method may include re-introducing an electrical current through the electrode after ablating the at least one identified target nasal nerve to confirm that target nasal nerve has been ablated.

In another aspect a method is provided for identifying a targeted nasal nerve associated with at least one symptom of rhinitis. The method may include inserting a stimulator probe into a nasal cavity, the probe having a probe shaft with a pair of electrodes disposed at a distal end of the probe shaft, positioning the distal end of the probe shaft so that the stimulating electrodes are adjacent to a nasal mucosa region, and introducing an electrical current through the electrodes via an electrical source coupled to the pair of electrodes such at least one nasal nerve underlying a nasal mucosa region in contact with the stimulating electrodes is stimulated. The method may further include measuring a response to the electrical current using the stimulating electrodes, repositioning the probe and stimulating the electrodes until a desired response is measured using the stimulating electrodes, and identifying the location of at least one target nasal nerve when the desired response is measured using the stimulating electrodes.

In many embodiments of the method, measuring the response includes measuring a parameter indicative of a change in at least one of nasal secretion and/or arterial blood flow. In some embodiments of the method, the parameter indicative of a change in at least one of nasal secretion and/or arterial blood flow includes at least one of electrical resistance and/or temperature. For example, measuring the response may include measuring a change in electrical resistance with the stimulating electrodes, the change in electrical resistance being indicative of a change in nasal secretion. The desired response may include a threshold change in electrical resistance measured after stimulating a targeted region with the electrodes.

In many embodiments particular types of nerves and desired regions may be targeted. For example, the targeted nasal nerve may be a parasympathetic nerve, and the tissue underlying the surface in contact with the stimulating electrodes is stimulated in the presence of an anesthetic that does not impact parasympathetic nerves. As another example, the desired region of the nasal mucosa may include a region of the nasal mucosa covering a medial pterygoid plate of a sphenoid bone.

In some embodiments of the method, the identified target nerve may be ablated. In some embodiments, the method further includes applying energy to a region adjacent to the targeted nasal nerve to ablate the targeted nasal nerve. For example, the identified target nerve may be cryogenically ablated. In many embodiments, the method further includes, after applying energy to the region adjacent to the targeted nasal nerve, stimulating the region adjacent to the targeted nasal nerve with the electrodes to confirm that the targeted nasal nerve has been ablated.

In many embodiments of the method, multiple locations of the targeted nasal nerve may be mapped so that a separate probe may be used to ablate each of the multiple locations. For example, the location of the targeted nasal nerve includes a first location of the targeted nasal nerve and the method further includes storing coordinates of the first location of the targeted nasal nerve, repositioning the probe and stimulating the electrodes until a desired response is measured at a second location of the targeted nasal nerve using the stimulating electrodes, and storing coordinates of the second location of the targeted nasal nerve. In some embodiments of the method, the method further includes positioning a cryoablation member disposed at a distal end of a second probe at the coordinates of the first location and cryogenically ablating the first location of the targeted nasal nerve, and positioning the cryoablation member of the second probe at the coordinates of the second location and cryogenically ablating the second location of the targeted nasal nerve. As an example, the stored coordinates of the first location and the second location and a current position of the cryoablation member are output on a display to guide positioning of the cryoablation member at the first and second locations.

In another aspect, a stimulator probe is provided for identifying and ablating at least one target nasal associated with at least one symptom of rhinitis. The probe may include a probe shaft having a proximal end and a distal end, at least two electrodes disposed at the distal end of the probe shaft, the at least two electrodes electrically coupled to an electrical source, wherein the electrodes are configured to electrically stimulate at least one nasal nerve underlying a nasal surface in contact with the electrodes in response to an electrical current generated by the electrical source, at least one sensor disposed on the probe, the sensor configured to detect a parameter indicative of a change in at least one of nasal secretion and/or arterial blood flow in response to the electrical current, and a processor operatively coupled to the electrical source and the sensor. The processor may be configured to control the electrical current generated by the electrical source, receive the parameter indicative of a change in at least one of nasal secretion and/or arterial blood flow from the sensor, and identify the at least one target nasal nerve based on the parameter indicative of a change in at least one of nasal secretion and/or arterial blood flow. The probe may further include an expandable ablation member configured to ablate the at least one identified target nasal nerve to reduce at least one symptom associated with rhinitis.

In many embodiments of the device, the electrodes may be designed and/or located to approach particular regions. For example, the electrodes may be disposed on the expandable ablation member. As a further example, the expandable ablation member may include an electrically non-conductive surface, and the at least two electrodes may be disposed on the electrically non-conductive surface of the ablation member. The expandable ablation member may be configured to inflate so as to position the at least two electrodes adjacent to a desired tissue region. In some embodiments of the device, the electrodes may be spaced apart in a range from 1 mm to 10 mm. For example, the electrodes may be spaced apart a sufficient distance to stimulate tissue 1-3 mm under the surface in contact with the electrodes.

In many embodiments of the device, the at least two electrodes are disposed on a distal tip that is releasably coupled to the probe shaft. The distal tip may include a connector that snaps to a connection portion of the probe shaft that is proximal of the expandable ablation member. The distal tip may extend from the connection portion to a distal end disposed distally of the expandable ablation member, and the at least two electrodes may be disposed at the distal end of the distal tip. In some embodiments, the distal tip may be made of polyamide or tempered stainless steel.

In many embodiments of the device, the probe shaft is sized so that the distal end of the probe shaft can reach a nasal mucosa covering a medial pterygoid plate of sphenoid bone through a passage of a middle nasal meatus from outside a nasal cavity.

In many embodiments of the device, the processor may control the electrical current. In some embodiments of the device, the processor may be configured to control at least one of a voltage, frequency, and/or pulse rate of the electrical current.

In many embodiments of the device, the sensor may detect certain parameters. The sensor may be configured to detect at least one of electrical resistance, temperature, and/or tumescence. For example, the sensor may be configured to detect a change in electrical resistance in an electrical signal passing through the electrodes after stimulation of the tissue, the change in resistance being indicative of a change in nasal secretion after stimulation of the tissue.

In another aspect, a system and method for adjusting neural stimulation of a target, such as a nerve, is provided. In many embodiments, the method includes electrically connecting at least one electrode to a first tissue, applying a stimulus to the at least one electrode, observing a response of a second tissue, identifying an electrode position on the first tissue wherein a desired response occurs on the second tissue when the stimulus is applied to the at least one electrode, and fixing the at least one electrode in place at the identified electrode position. In certain embodiments, the stimulus applicator is disposable. The stimulus can be a voltage signal, a current signal, and can be preprogrammed. In certain embodiments, the voltage or current signal is a controlled voltage or a controlled current signal. In other embodiments, an estimated minimum stimulus is calculated, and in yet another embodiment a stimulus profile is generated. The stimulated tissue may nerve tissue or mucosal tissue. Examples of a desired stimulus response include a change in airway patency, at least partial blockage of a neural impulse, and the initiation of at least one neural impulse. A response can be directly or indirectly observed, either visually or with instrumentation.

In another aspect, a neural stimulation system is provided. The system may include at least one electrode electrically connected to a first tissue, means for applying a stimulus to the at least one electrode, means for observing a response of a second tissue, means for identifying an electrode position on the first tissue wherein a desired response occurs on the second tissue when the stimulus is applied to the at least one electrode, and means for fixing the at least one electrode in place at the identified electrode position.

In still another aspect, a computer program product may include a computer readable medium having stored thereon computer executable instructions that, when executed on a computer, causes the computer to perform a method of neural stimulation, including the steps of applying a stimulus to at least one electrode electrically connected to a first tissue, observing a response of a second tissue, and identifying an electrode position on the first tissue, wherein a desired response occurs on the second tissue when the stimulus is applied to the at least one electrode.

In another aspect, a neural stimulation system is provided. The system may include at least one electrode electrically connected to a first tissue, a gross adjustment stimulator coupled to and delivering a stimulus to the at least one electrode, a stimulus measurement subsystem in communication with the gross adjustment stimulator and having at least one sensor, the at least one sensor measuring a response of a second tissue, and a programming subsystem in communication with the stimulus measurement subsystem, the programming subsystem collecting data from the group consisting of stimulus data and tissue response data.

In many embodiments, the systems and methods can be used to identify autonomic nerves through a layer of overlying tissue (1-10 mm), with a specific application in localizing the posterior nasal nerves transmucosally in the nasal cavity. In some embodiments, the apparatus may include an expandable structure made of an electrically non-conductive material attached to a cannula long enough to reach the nasal mucosa that covers the medial pterygoid plate of the sphenoid bone through the passage of the middle nasal meatus from the exterior of the body.

In many embodiments, the expandable structure may be a balloon. On the outer surface of the balloon, there may be at least two electrodes that are connected to a source of electricity which can be direct or alternating current. For example, the current may pass between the two electrodes through the underlying tissue. The electrodes may be arranged in a mono-polar or bipolar arrangement. In some embodiments, more than two electrodes may be used. For example, the more electrodes that are on the surface of the balloon, the more precisely the location of the nerves may be identified. However, there is also an upper limit of the number of electrodes on the balloon, because electrodes that are close together may not send electrical signals as deep into the mucosa. In addition, the pair of electrodes may be disposed on the exterior of the cannula in the general vicinity of where a nasal turbinate would be.

In many embodiments, the electrodes may be made of any conductive material, such as silver or zinc. In many embodiments, the electrodes may be any shape, such as a circle or square, and may be adhered to their respective surfaces by means such as adhesive, printing, thermal fusion, silver pen, or copper tape.

In many embodiments, the electrodes may be attached by their respective wires that run parallel to the cannula and connect to a processor that is located outside of the nasal cavity. In many embodiments, the processor may deliver electric pulses through the electrodes by way of the underlying tissue. In some embodiments, the processor may have the capacity to alter the voltage, frequency, pulse rate, and current of the electrical signal, as there are optimal ranges for nerve stimulation. In addition, the stimulator may use varying percentages of duty cycles for the most effective stimulation of the nasal nerves. The minimum pulse duration for effective nerve stimulation is at least 0.03 microseconds, and all autonomic fibers have a probable low discharge rate of around 1-2 imp/sec (Folkow, 1955). Research has suggested that the frequency-dependent increase in nasal secretion and increased arterial blood flow for parasympathetic nasal nerves is observed when stimulations are within the range of 0.5-12 impulses per second, with the minimal effective frequency between 2-5 imp/sec and a maximum secretion at 15 imp/sec (Anggard). The minimal effective frequency for the aforementioned responses is between 2 and 5 hertz, with a maximum of 10 to 15 hertz (Eccles and Wilson). Transcutaneous electrical nerve stimulation (TENS) is also a common practice, suggesting that electrical stimulation of the nasal nerves is feasible over the mucosa. Although there is no published research concerning the response time between electrical stimulation and nasal secretion, the reaction is visibly noticeable. Presumably, the closer the electrode is to the targeted nasal nerve, the more the nasal secretions would be visible.

In many embodiments, the processor may electrically stimulate specific regions of the nasal cavity, which are defined by activating different pairs of electrodes on the surface of the balloon. When the region that is closest to the targeted nerve is activated, the change in nasal secretion and arterial blood flow may be at their greatest. The two electrodes attached to the exterior of the cannula are designed to track this change in nasal secretion through measuring resistance, temperature, degree of tumescence or other parameters. Mucus contains a variety of electrolytes that are capable of conducting electricity, so as nasal secretion increases, in many embodiments, the two electrodes on the cannula that are in contact with a nasal turbinate can track and record the decrease of resistance in the electrical signal. When the resistance is at the lowest, the pair of electrodes that were just activated are in the nearest vicinity of the targeted nerves.

The foregoing presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

BRIEF DESCRIPTION OF THE DRAWINGS

FIG. 17 shows electrical stimulation parameters.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
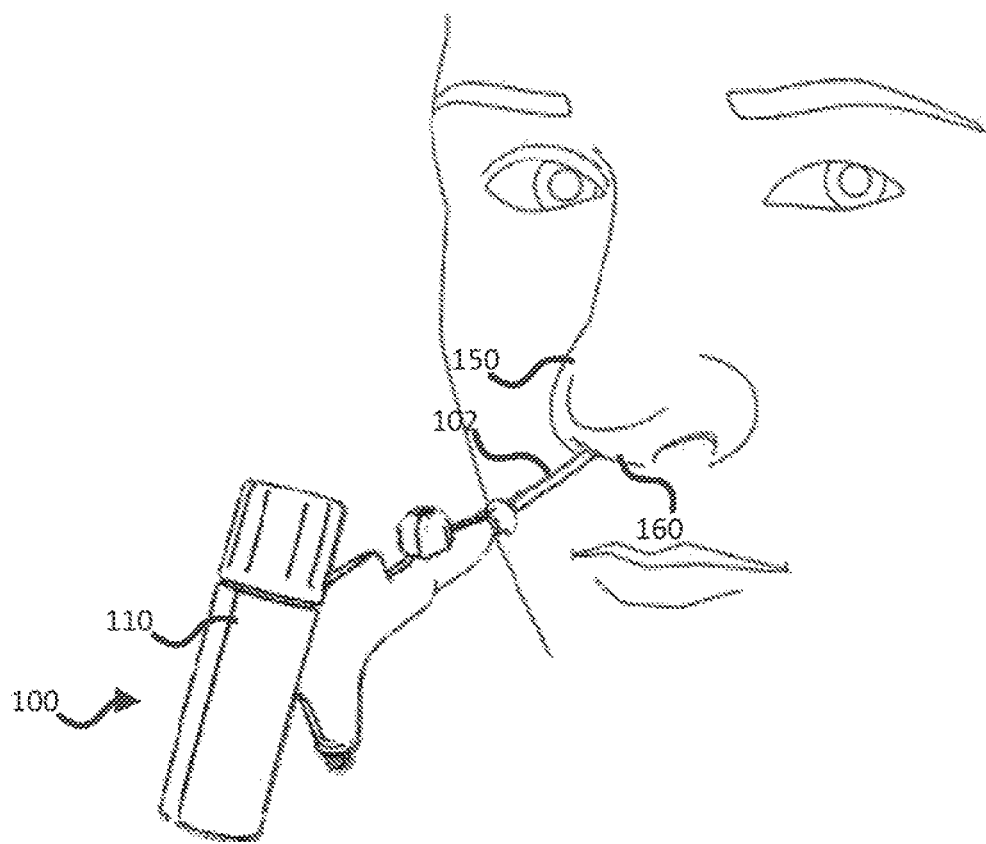
FIG. 1 shows a device 100, in accordance with many embodiments.

FIG. 1 shows a device 100, in accordance with many embodiments. As can be seen in FIG. 1, device 100 may include a hand piece 110 and cannula or probe shaft 102 which is shown after it is inserted in the nasal cavity 160 of a subject's nose 150. Although device 100 will be described in further detail below, it can be understood that device 100 may be designed so that cannula or probe shaft 102 is long enough to reach a desired tissue location when hand piece 110 is placed outside of nasal cavity 160 as shown. In some embodiments, the user may place the tip of device 100 over a target area under endoscopic guidance. By putting lateral pressure on the tip of the device 100, intimate contact with the desired tissue location can be assured. The user may verify the contact of the electrodes with the mucosal surface by using the endoscope (not shown in FIG. 1). In some embodiments, it may be desirable to use device 100 without an endoscope, as will be described in further detail below.

Figure 2:
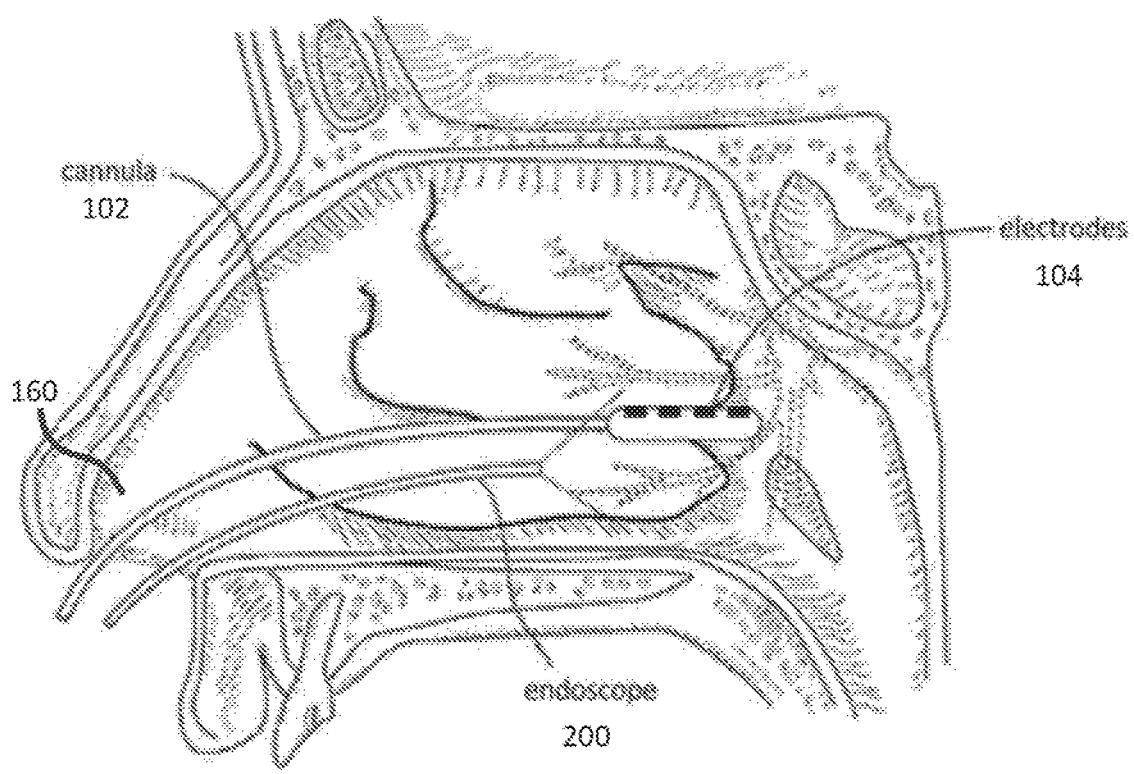
FIG. 2 shows a sagittal view of a human head with the device and the endoscope in the nasal cavity, in accordance with many embodiments.

FIG. 2 shows a sagittal view of a human head with the device 100 and the endoscope 200 in the nasal cavity 160, in accordance with many embodiments. As can be seen in FIG. 2, a number of stimulating electrodes 104 may be disposed at the distal end of the device 100 and may be placed over a target tissue area. Operation of a system with device 100 with stimulating electrodes 104 to stimulate and identify a target nerve will be described with further reference to the figures below. It can be seen from FIG. 2 that cannula 102 and electrodes 104 are configured to reach a targeted location within the nasal cavity to effect the desired stimulation and identification of target nerves. For example, cannula 102 and electrodes 104 may be configured to reach a region of the nasal mucosa covering a medial pterygoid plate of sphenoid bone through a passage of a middle nasal meatus while handpiece 110 is outside of the nasal cavity so as to target a posterior nasal nerve.

Figure 3:
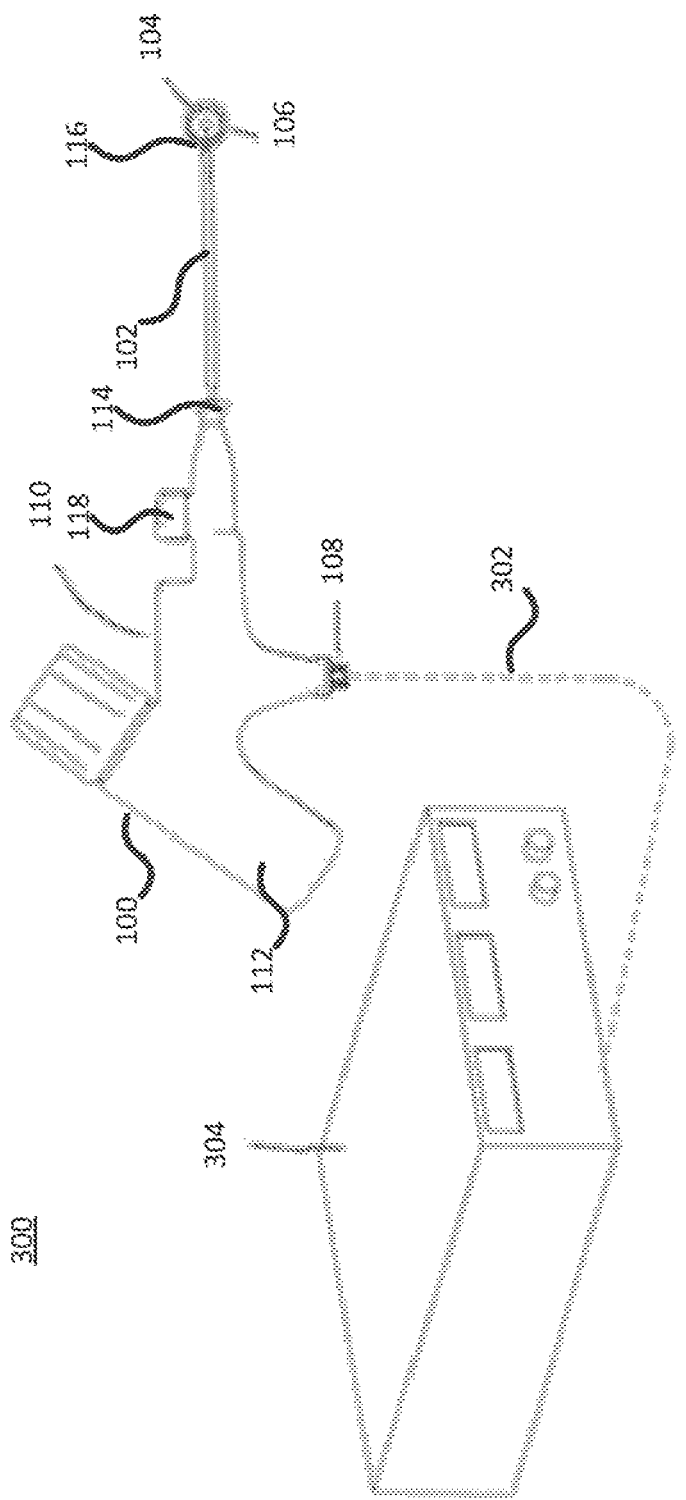
FIG. 3 shows a system 300, in accordance with many embodiments.

FIG. 3 shows a system 300, in accordance with many embodiments. As can be seen in FIG. 3, system 300 may include device 100 described above. Specifically device 100 may include device handle 110 which may be connected to the cannula 102 and to an end effector 106. Cannula 102 may have a proximal end 114 and a distal end 116 at which end effector is disposed. The end effector 106 may carry the nerve stimulating electrodes 104 on a surface thereof. As will be described in further detail below, end effector 106 may also incorporate an ablation member. For example, end effector may incorporate a cryoablation member, an RF ablation member, or any other suitable energy modality to ablate nerves. The device handle 110 may also be connected to an electrical source 304 via a standard signal connector 108, which may interface with any suitable cord 302. In this embodiment, the system 300 may be used by electrically connecting the device handle 110 to the electrical source 304 via any suitable electrical connection such as a cord 302 with a connector that connects to a standard signal connector 108. Electrical source 304 may provide a current through electrodes 104 to stimulate tissue, nerves, or other areas in contact with the electrodes 104.

As described above, since parasympathetic nerves, such as the posterior nasal nerve may respond to electrical stimulation with increased nasal secretion or blood flow, the response to stimulation may be used to identify a target nerve associated with secretory or vascular changes in tissue innervated by the target nerve with system 300. Specifically, in order to identify the target nerve, the end effector 106 may be placed over the region that the nerve(s) may be located, the electrical source 304 may provide a current through electrodes 104 to stimulate the region, and the response can be observed to determine whether the target nerve has been located. Although this operation is explained below with reference to identifying nasal nerves that may be associated with one or more symptoms of rhinitis, it will be understood that this only illustrative, and that embodiments may be directed to identifying other nerves associated with secretory or vascular changes in tissue innervated by the target nerve.

In some embodiments, if the targeted nerve is a posterior nasal nerve (which may be associated with one or more symptoms of rhinitis, e.g.), then end effector 106 may be positioned in a general region where the posterior nasal nerve is expected. To avoid the need for visualization, this may be determined based on an anatomical landmark. For example, end effector 106 may be placed adjacent to nasal mucosa covering a medial pterygoid plate of a sphenoid bone. Once positioned, the end effector 106 may be pressed upon the target tissue area, and the electrical source 304 can activate the electrical current through electrodes 104. In order to determine whether the nerve has been located, the user may observe the tissue which is innervated by the nerves that are being stimulated. For example, the user may observe the turbinate while stimulating the nasal tissue region. An increased flow of secretions from the surface of mucosa or swelling of the turbinates may indicate that the nerve has been located. If no increased secretion or swelling is identified, it may be determined that the nerve has not been adequately located. Once the target nerve is located, the user can proceed to treat the nerve as desired to induce a change in the secretory or vascular response of the tissue. For example, in the case of the posterior nasal nerve as described above, the user may ablate the nerve so as to reduce the symptoms of rhinitis.

Although the target nerve may be identified by observing a response as described above, it will be understood that in some embodiments, a response may be measured to identify the target nerve. It will be understood that the increased secretion or vascular response may be determined by measurement of various parameters. For example, sensors (not shown in FIGS. 1-3) may measure resistivity, conductivity, or temperature in the target region to determine whether the desired response associated with the target nerve has occurred, since secretion and/or vascular response may cause particular changes with such parameters. As an example, since mucous typically contains electrolytes that are capable of conducting electricity, increased nasal secretion may be expected to result in decreased resistance in an associated region of the nose. Thus, the resistivity can be measured in the region during stimulation and a particular resistivity or change in resistivity may indicate that the electrodes are located in the nearest vicinity of the target nerves. Similarly, the temperature in the region may increase in response to a particular vascular response that results from stimulation of the targeted nerve, and temperature may be measured to determine whether the electrodes are in the vicinity of the targeted nerve.

In some embodiments, end effector 106 itself may be used as an ablation member as described above. For example, end effector 106 may be used to cryogenically ablate a target nerve. A cryogen may be stored in handle 110 at 112 and may be fluidly coupled via cannula 102 to the end effector. Cryogen may be introduced to end effector from housing 112 via control valve 118 to ablate regions surrounding end effector 106. End effector 106 may be configured to expand in response to introduction of cryogen. If end effector 106 is not a cryogenic member, end effector may still be configured to expand for reasons described herein. For example, end effector 106 may expand so as to position electrodes 104 in a desired location as will be described further below. In some embodiments, another device or treatment may be used to treat the located nerve. For example, the nerve may be ablated using a separate ablation device, which may be a cryogenic ablation device, an RF ablation device, or any other device using any other suitable energy to ablate the nerve.

Figure 4:
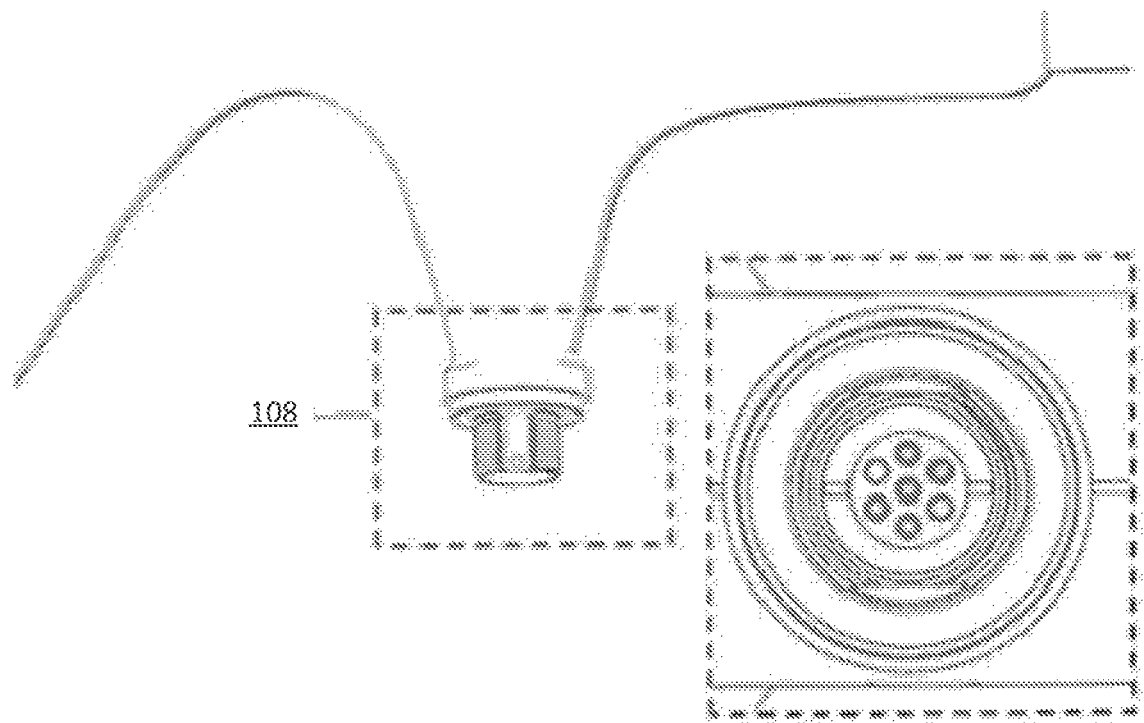
FIG. 4 shows connector 108 of device 100, in accordance with many embodiments.

FIG. 4 shows connector 108 of device 100, in accordance with many embodiments. As can be understood with reference to FIG. 4, impulses and return signals of the nerve stimulating elements may be routed from elements inside the nasal cavity to the connector 108 at the bottom of the handle, where the stimulator 304 connects. In some embodiments, return signals may include signals from the electrodes or other sensors disposed on cannula 102 for measuring the response to stimulation as described above.

Figure 5:
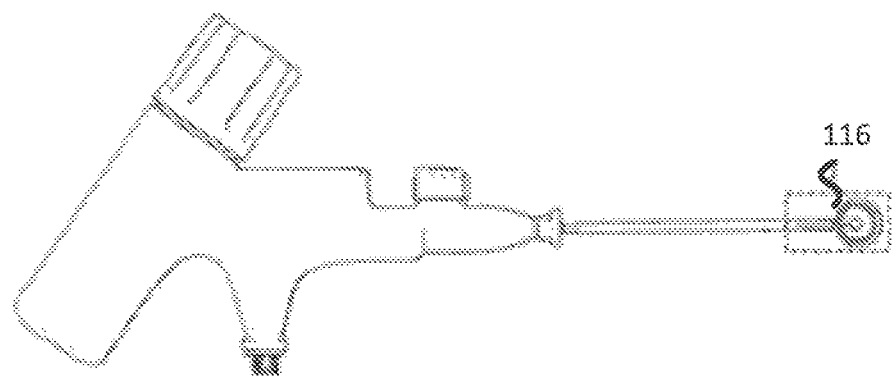
FIG. 5 shows distal end of device 100, in accordance with many embodiments.

FIG. 5 shows distal end 116 of device 100, which, as described above may include nerve stimulating elements and ablation members, in accordance with many embodiments. It will be understood that the nerve stimulating elements can be in various arrangements depending on the desired application and can be affixed to the distal end 116 of the device in various ways. For example, stimulating elements may be embedded elements that can be applied to the exterior surface of the probe at the distal end 116 via metallic ink or thin metallic film. A number of arrangements of stimulating elements that may be used with device 100 are described below with reference to FIGS. 6-10.

Figure 6:
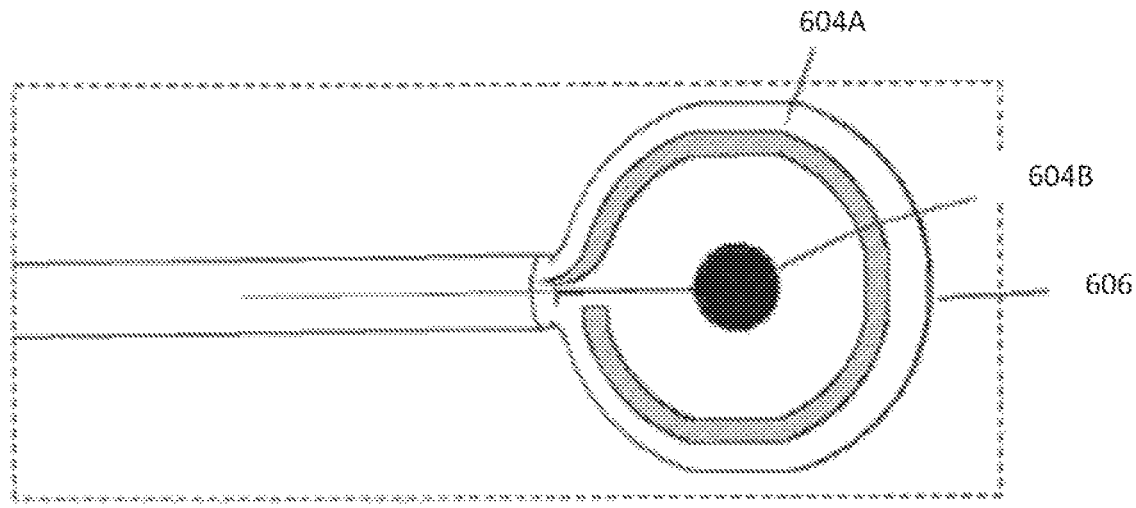
FIG. 6 shows an end effector 606 in accordance with many embodiments.

FIG. 6 shows an end effector 606 with electrodes 604A and 604B in accordance with many embodiments. As can be seen in FIG. 6, end effector 606 may have a center electrode 604B disposed centrally on end effector 606 and an outer electrode 604A that is disposed along the perimeter of end effector 606 so as to surround center electrode 604B. In operation, an electrical signal may be passed (from electrical source 304 for example) to the center electrode 604B. The signal may then pass through the tissue in contact with center electrode 604B and then to the outer electrode 604A. In this fashion, any nerves which may fall in the area between the circular outer electrode 604A and the center electrode 604B will receive the current and be stimulated. It will be understood that the distance between outer electrode 604A and center electrode 604B may dictate the depth of stimulation. Thus, the distance may be selected so as to approach the targeted nerve. For example, the distance between electrodes 604A and 604B may be a predetermined distance so as to achieve a depth of stimulation of 1 to 5 mm. In some embodiments, the distance may be selected so as to achieve a depth of stimulation of 1 to 3 mm. To achieve such a depth, it may be desirable to provide a separation distance of about 1 mm to 10 mm.

Figure 7:
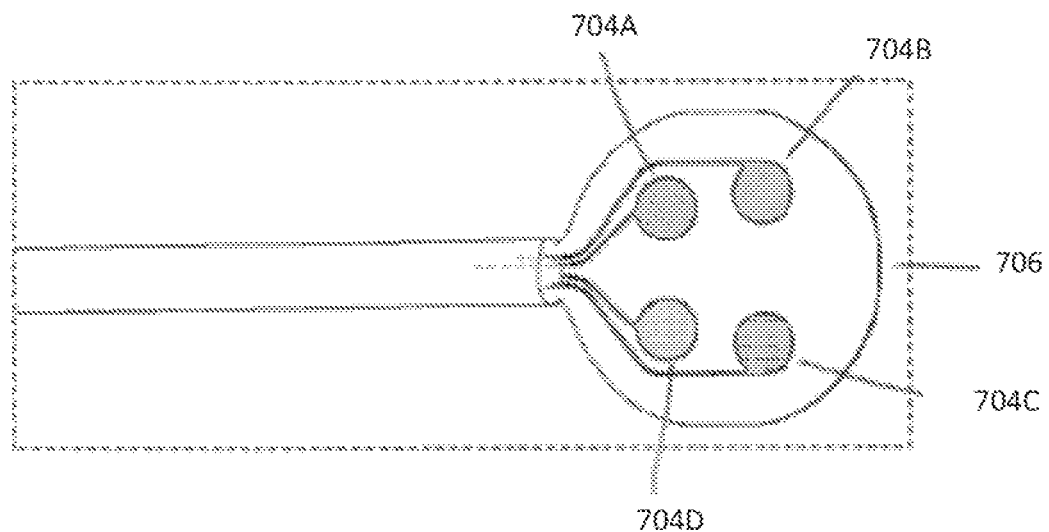
FIG. 7 shows an alternate end effector 706 in accordance with many embodiments.

FIG. 7 shows an alternate end effector 706 in accordance with many embodiments. As can be seen in FIG. 7, end effector 706 may include four electrodes 704A-D as opposed to two electrodes. It will be understood that all four electrodes 704A-D may be coupled to electrical source 304 so that current may be directed through any or all of the electrodes 704A-D. The current will pass through the tissue between whichever electrodes are activated and stimulate any intervening nerves as described above. This arrangement may allow a user to selectively stimulate certain areas in contact with end effector 706 to more precisely stimulate and identify/locate a target nerve. For example, depending on which electrodes are used and the observed or measured response to stimulation therein, a location in any one of four quadrants on the end effector may be determined, which may provide a more defined location of the nerve than using one or two electrodes. It will be understood that although multiple electrodes are used in a so-called bipolar arrangements, in some embodiments, a single electrode may be used to stimulate and identify a nerve.

Figure 8:
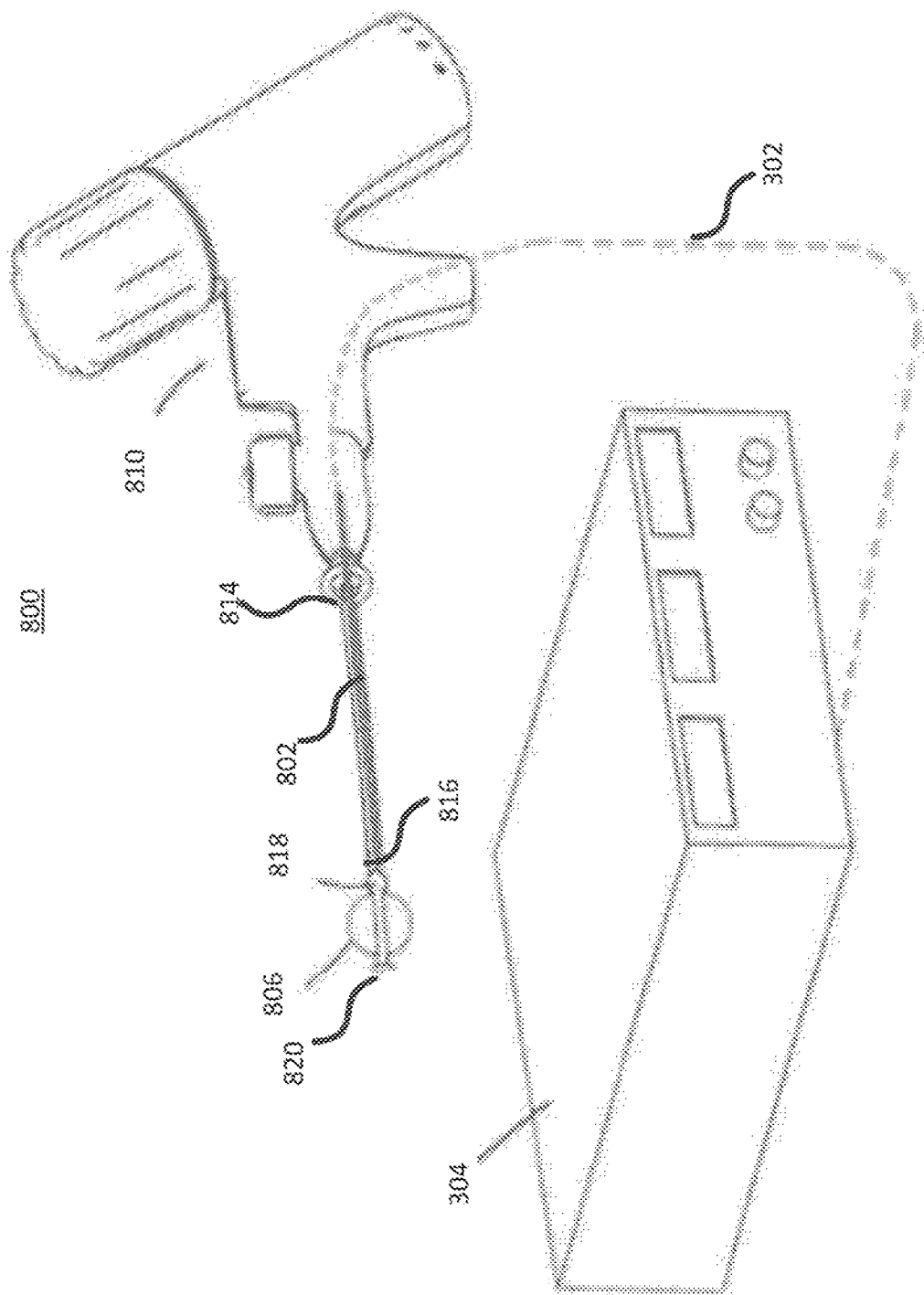
FIG. 8 shows a system 800 with a reusable stimulator tip 818 in accordance with many embodiments.

FIG. 8 shows a system 800 with a reusable stimulator tip 818 in accordance with many embodiments. Reusable stimulator tip 818 may be releasably coupled from the cannula 802 of probe 810 which may be desirable, for example, to clean the stimulator between human uses. Specifically as seen in FIG. 8, reusable stimulator tip 818 may be clicked onto the distal end 816 of the cannula 802 when in use, and may be pulled off when not in use. When connected to cannula 802, reusable stimulator tip may extend past the energy probe 806 (which may be, e.g. a cryogenic ablation member or any other type of ablation member as described above with respect to end effector 106) on the side that will not be in contact with the lateral wall of the nasal cavity. Electrodes on reusable stimulator tip may be disposed at the distal tip 820 which may extend just distally of the energy probe 806, as will be described below with respect to FIGS. 9A-9C. It can be seen that reusable stimulator tip 818, once clicked onto the cannula 802 may connect to the stimulator 304 via a low profile cable 302 that runs externally but adjacent to the cannula 302 of the device handle 810. The electrodes 804 (not shown in FIG. 8) of the reusable stimulator tip 818 may be positioned on the distal end facing perpendicular to the plane of the end effector 806, as will be described with reference to FIGS. 9A-9C.

Figure 9A:
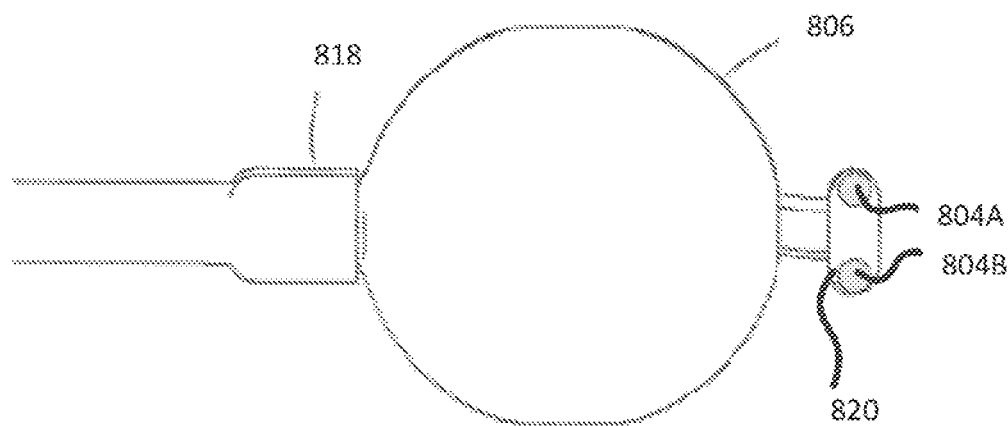
FIGS. 9A-9C show views of reusable stimulator tip 818 and end effector 806 in accordance with many embodiments.
Figure 9B:
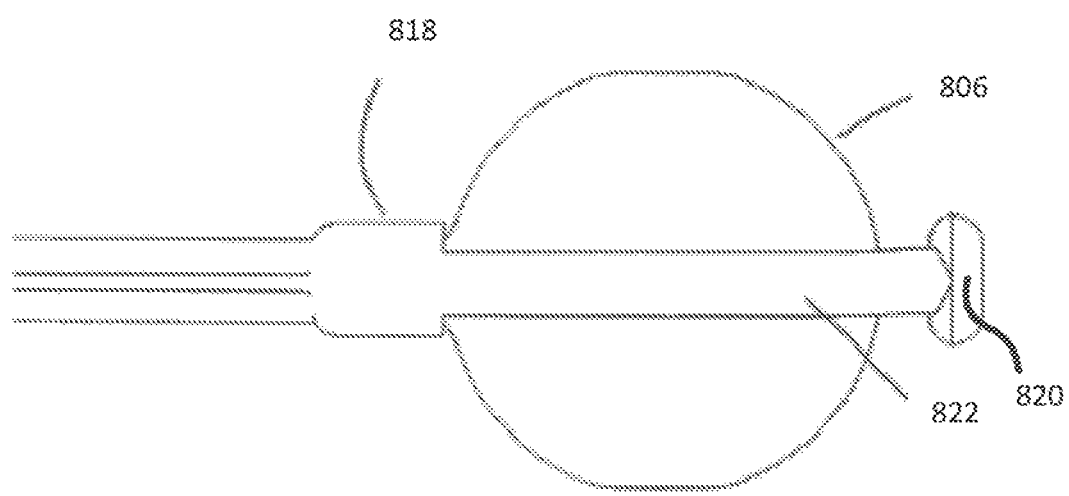
Figure 9C:
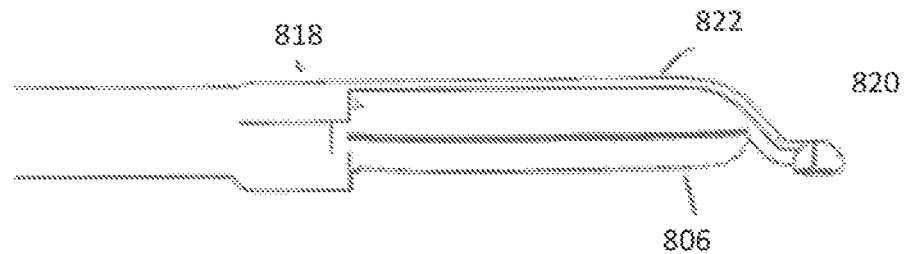

FIGS. 9A-9C show views of reusable stimulator tip 818 and end effector 806 in accordance with many embodiments. FIG. 9A shows a top view of the assembly 818 when coupled to cannula 802 and end effector 806, and FIG. 9B shows the bottom view of the assembly 818 when coupled to cannula 802 and end effector 806. FIG. 9C shows the side profile of reusable stimulator tip 818 affixed to cannula 802 and end effector. As can be seen in FIGS. 9A-9C, reusable stimulator tip 818 only extends along one side of end effector 806 so as not to interfere with a side of end effector 806 during operation. As can be particularly seen in FIG. 9C, reusable stimulator tip 818 hugs a bottom surface of end effector 806 so as not to increase the profile of the probe when inserted into the target region. The portion extending along the bottom of end effector 806 may be a lever spring arm 822.

Lever spring arm 822 may end at a distal tip 820 which is disposed distally of the end effector 806. In some embodiments, electrodes 804A and 804B may be disposed at the distal tip 820 of lever spring arm 822, as shown in FIGS. 9A and 9B. Although shown as two spaced apart electrodes, any suitable arrangement of electrodes may be used at distal tip 820 as described above. For example, distal tip 820 may be designed to extend along a larger portion of the perimeter of end effector 806 and a number of electrodes may be provided thereon. Lever spring arm 822 may be spring biased to keep distal tip 820 and electrodes 804A and 804B in contact with the desired region of tissue when in use.

Figure 10:
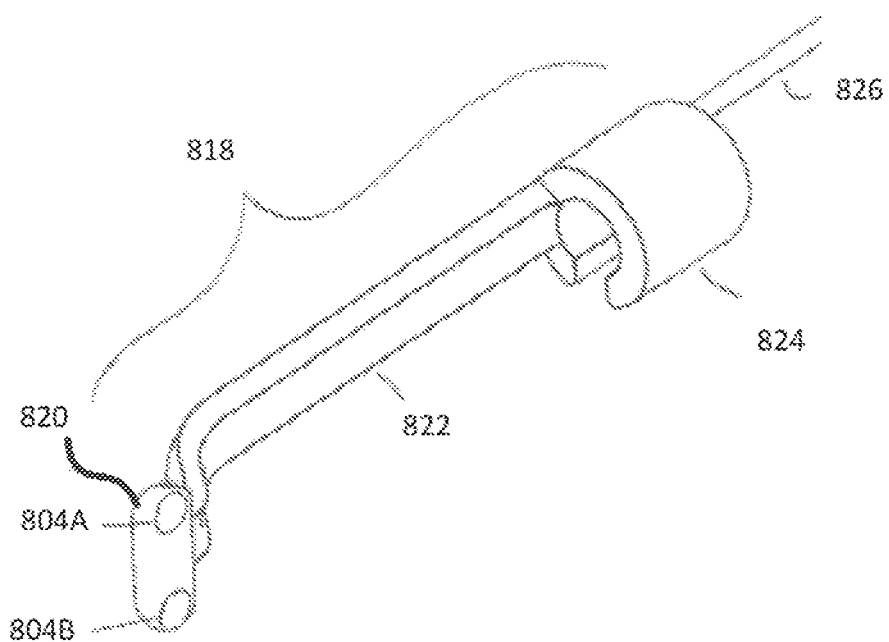
FIG. 10 shows reusable stimulator tip 818 in accordance with many embodiments.

FIG. 10 shows reusable stimulator tip 818 unattached to device 810 in accordance with many embodiments. As can be seen in FIG. 10, the electrodes 804A and 804B of the stimulator tip 818 may be positioned on the distal end 820 facing perpendicular to the plane of the stimulator tip 818. As described above, the stimulator tip 818 is designed to ensure the electrodes 804A and 804B stay in positive contact with the mucosal lining throughout use in the nasal cavity once clicked onto the cannula 802 by using a lever spring arm 822 also shown illustrated in FIG. 10. In some embodiments, the stimulator tip 818 can be made out of an injection moldable semi-rigid plastic (i.e. polyimide) or a tempered stainless steel. For example, the semi rigid plastic or stainless steel along with the geometry of the arm 822 may create a positive lateral force to ensure the electrodes 804A and 804B contact the relevant tissue (e.g. the mucosa) while positioning the probe for stimulation. As described above, the reusable stimulator tip 818 is designed to hug the energy probe 806 to minimize the added profile to ensure distal portion of the instrument can navigate around the structures in the nasal passageway.

As can be seen in FIG. 10, reusable stimulator tip 818 may include a connector 824 that snaps onto cannula 802. Although shown as a snap-on connector that may wrap around cannula 802, it will be understood that connector 824 may include any suitable connector for connecting to cannula 802 as described. In order to electrically couple stimulating electrodes 804A and 804B to an electrical source, the proximal end of reusable stimulator tip 818 may include a low-profile cord 826 electrically coupled to the electrodes 804A, 804B and configured to be electrically coupled to the electrical source 304. Cord 826 may be connected to or a part of cord 302 described above with respect to FIG. 8, and may run externally along (but adjacent to) cannula 802.

Figure 11:
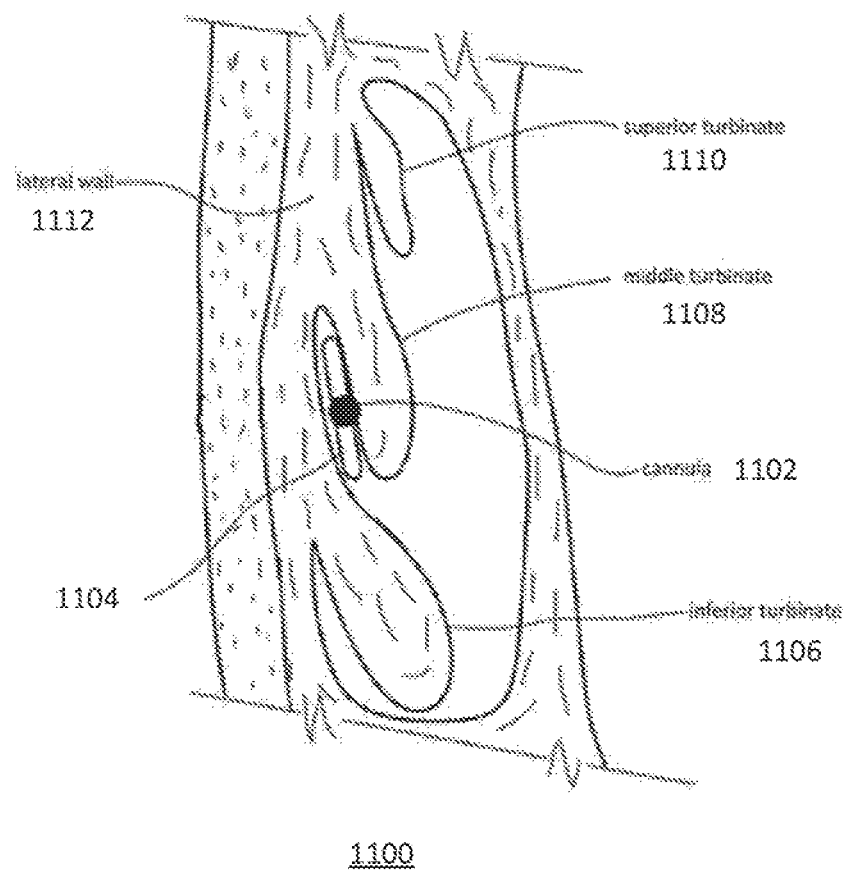
FIG. 11 shows a coronal view of the relative location of an end effector with respect to anatomical landmarks in the nasal cavity, in accordance with many embodiments.

FIG. 11 shows a coronal view of the relative location of an end effector 1104 with respect to anatomical landmarks in the nasal cavity, in accordance with many embodiments. As can be seen, in some embodiments, it may be desirable to target a location between a middle turbinate 1108 and lateral wall 1112 by positioning end effector 1104 therein. This location may allow targeting of a nasal nerve such as the posterior nasal nerve, which is associated with symptoms of rhinitis, as described above. It can be seen that in some cases the target location may require a low profile device as described above.

Figure 12A:
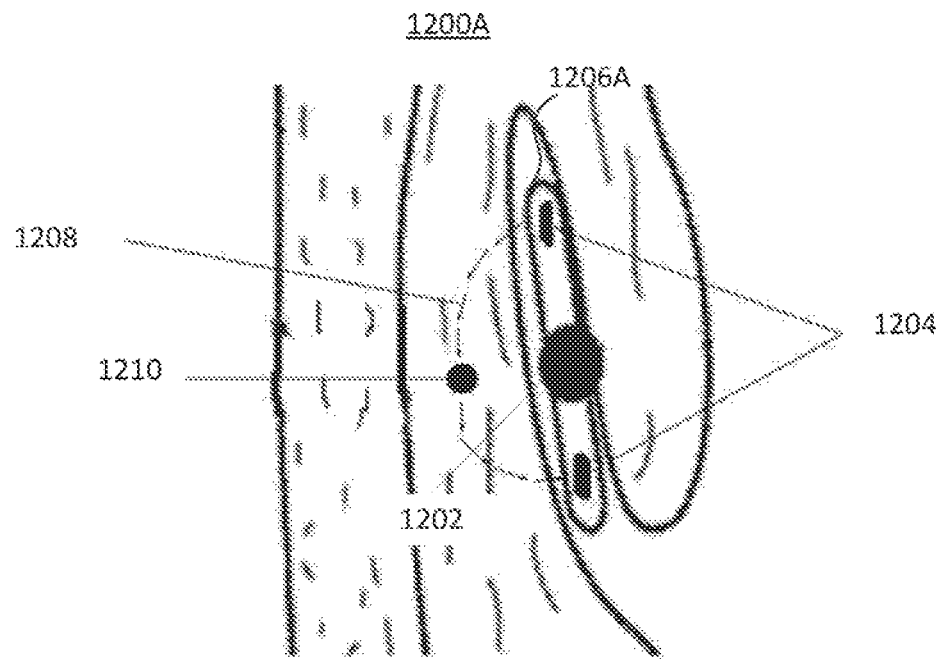
FIG. 12A shows a diagram tracing the current flow through the tissue that stimulates the nerve, in accordance with many embodiments.
Figure 12B:
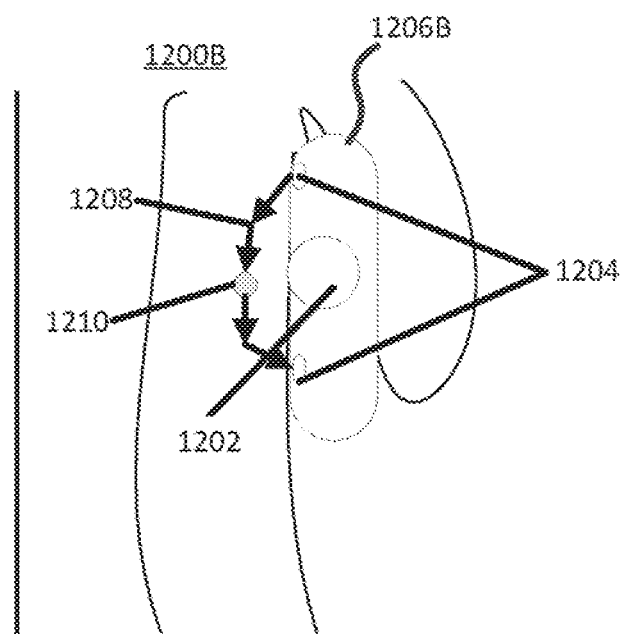
FIG. 12B shows the diagram of FIG. 12A with an expandable member in an inflated position, in accordance with many embodiments.

FIG. 12A shows a diagram tracing the current flow through the tissue that stimulates the nerve, in accordance with many embodiments. As can be seen in FIG. 12A, the distance between electrodes 1204, which may be disposed on end effector in the deflated state 1206A may be selected to achieve a desired depth of stimulation so that current 1208 reaches a targeted nerve 1210. In some embodiments, end effector may be inflated into its inflated position 1206B as described previously. FIG. 12B shows the diagram of FIG. 12A with end effector in its inflated position 1206B, in accordance with many embodiments. It can be seen that putting end effector in its inflated position 1206B may allow electrodes 1204 to be more closely in contact with the targeted nerve 1210. This may allow for a more pronounced effect when stimulating and/or ablating the targeted nerve 1210.

Figure 13:
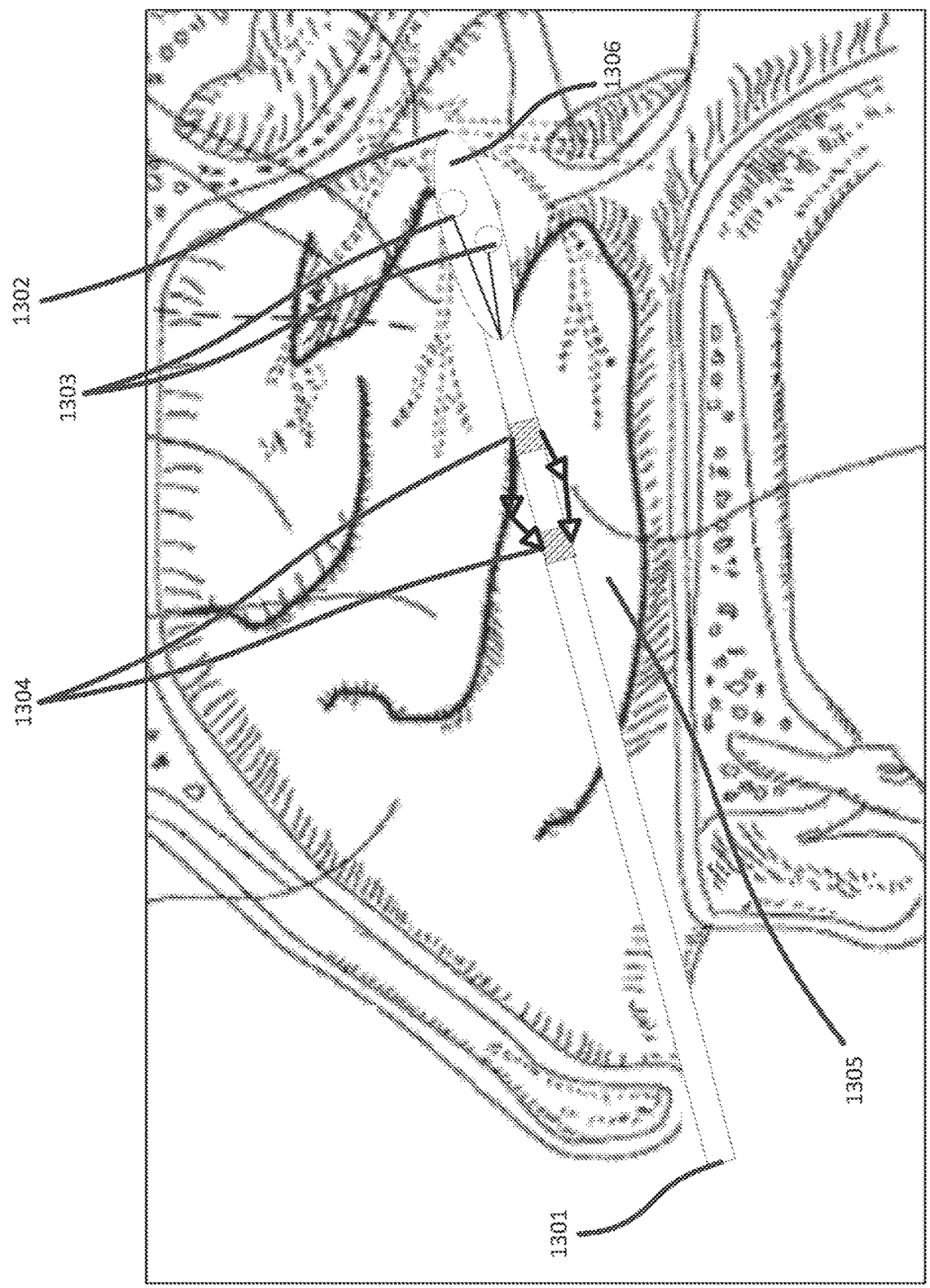
FIG. 13 shows a system with conductivity sensors in accordance with many embodiments.

FIG. 13 shows the distal end of a probe 1301 with conductivity sensors 1304 in accordance with many embodiments. As can be seen in FIG. 13, the distal end 1302 of probe 1301 may be placed in contact with a desired region expected to be innervated by the target nerves. For example, the distal end 1302 may be positioned to contact a region expected to be innervated by a posterior nasal nerve. In order to identify and locate the targeted nerve, electrical current may be provided to stimulating electrodes 1303. Rather than rely on an observed response to the stimulation, in some embodiments, probe 1301 may include conductivity detectors 1304. Detectors 1304 may be located proximally of the stimulating electrodes 1303 so as to detect conductivity in a desired region proximal of the nerve. For example, stimulation of a nerve may result in secretion at a proximal location of the stimulation, so it may be desirable to locate the conductivity detectors accordingly. As can be seen in FIG. 13, conductivity sensors may be configured to detect conductivity between two points, which conductivity may be indicative of increased secretion as described above. Although not shown here, conductivity sensors 1304 may be coupled to a processor and associated computing device that may be able to monitor the conductivity in response to stimulation and determine when the stimulating electrodes are suitably close to a target nerve. The computing device may be configured to alert the user when a target nerve is identified using any suitable alert including a visual alert, an audio alert, or a haptic alert. Although shown here as conductivity sensors, sensors 1304 may be any suitable sensor to measure any of the parameters described herein that may indicate increased secretion or a desired vascular response. For example, temperature sensors or other sensors may be used in place of or in addition to conductivity or resistivity sensors. Any of the sensors described herein to measure the response to stimulation may be located anywhere on probe 1301. For example, sensors may be embedded onto electrodes 1303 or on other portions of the end effector 1306.

In some embodiments, it may be advantageous to use separate devices for nerve identification and ablation. For example, if multiple locations of ablation are required, it may be beneficial to first identify and map all of the nerve locations and then perform ablation. This may be beneficial because ablation after an initial target nerve is located may affect sensing other target nerves in the vicinity. This may also be beneficial because the user would be able to use a very small tip diameter, between 0.5 mm and 5 mm to map the locations of the nerves as described before which may provide improved precision and/or resolution. Accordingly, image guided navigation systems and methods for identifying target nerves are described according to many embodiments.

Figure 14:
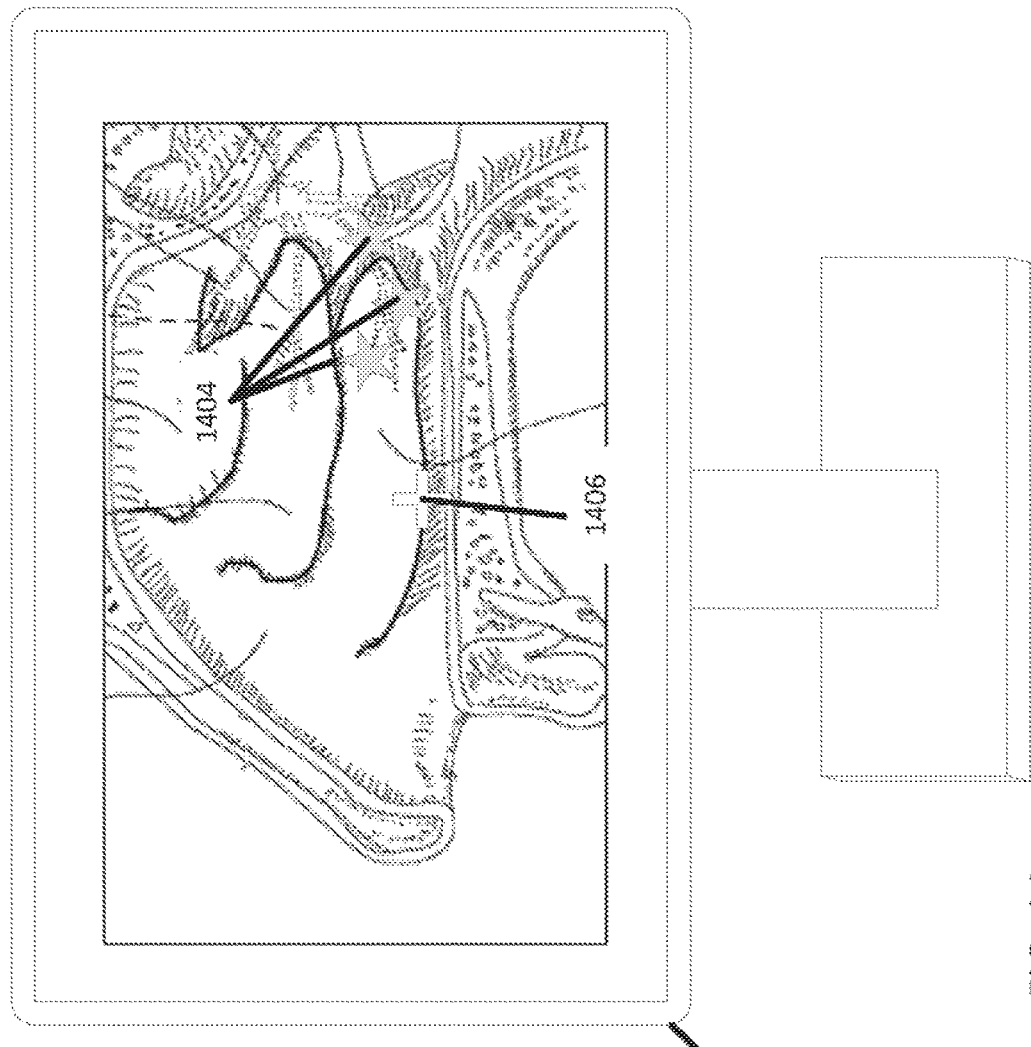
FIG. 14 shows an image guided navigation system for ablation in accordance with many embodiments.
Figure 14:
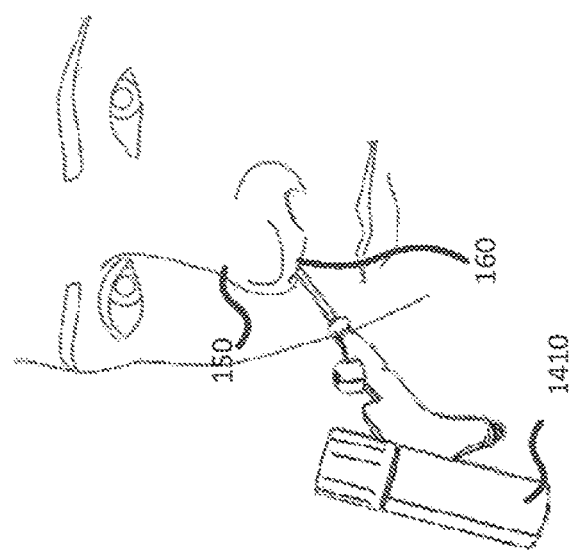

FIG. 14 shows a simplified illustration of an image guided navigation system for ablation in accordance with many embodiments. In some embodiments, the navigation system would place a mark on each target location during the nerve detection step so that the location can be easily and precisely identified subsequently with an ablation device. The system may store coordinates of each identified target location and display them on an image for subsequent ablation. As seen in FIG. 14, once the locations have been determined, a display 1402 may show the user the identified target locations 1404 and the current location 1406 of the ablation probe attached to device 1410 in real time. This would allow the user to use one device to identify multiple target locations 1404 without affecting other areas in the same vicinity by ablation thereof. Once stored, the user may use the image guidance with the current location of the ablation probe 1406 shown in real time and the identified target nerve locations 1404 to easily and precisely ablate the target locations. In some embodiments, the ablation tip may not have electrodes on it. It can be seen that by tracking the ablation device with the guidance system, the proper target locations can be approached, contacted and ablated.

Figure 15:
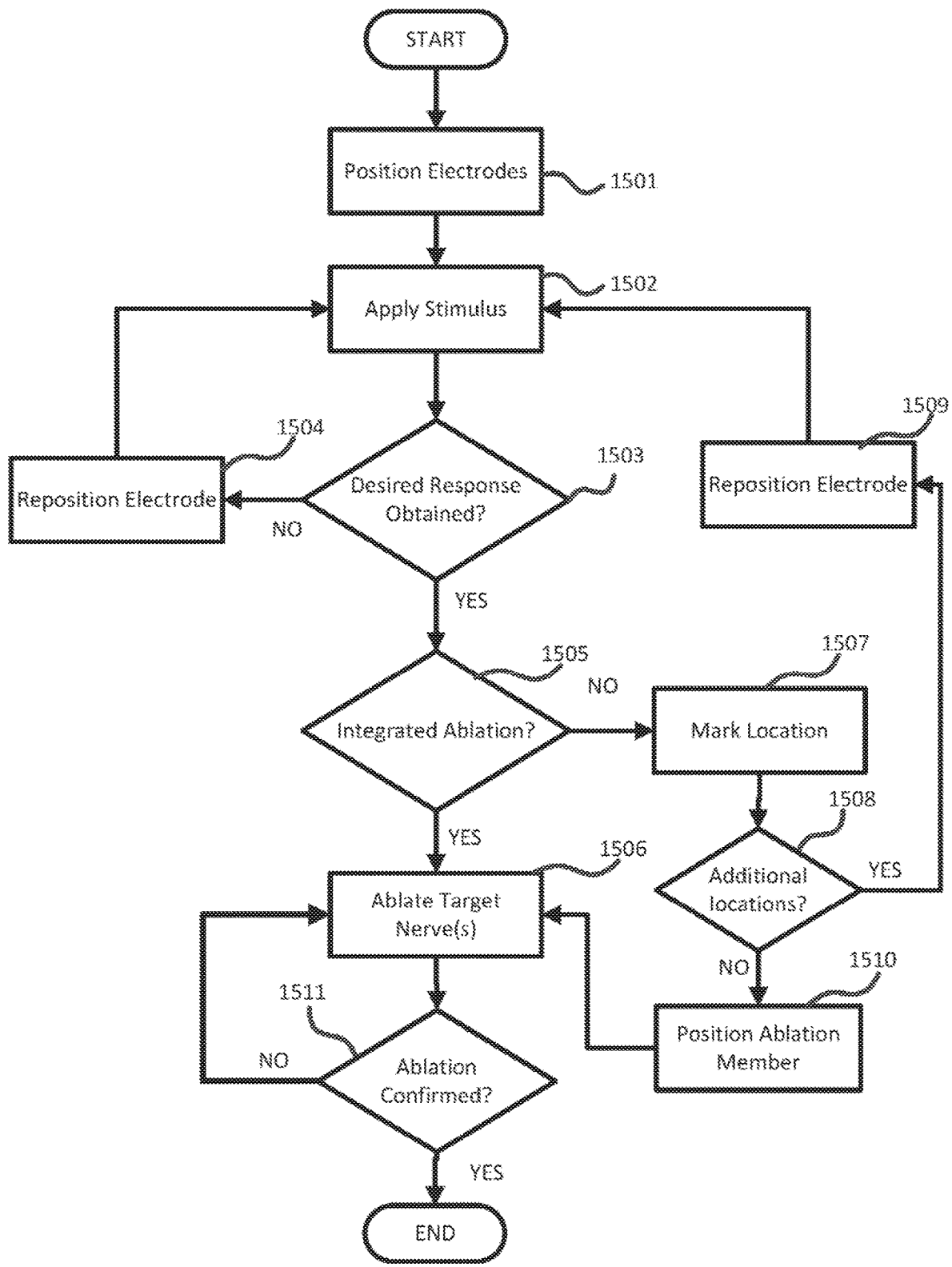
FIG. 15 shows a flowchart describing a method of nerve localization, in accordance with many embodiments.

FIG. 15 is a flowchart illustrating a method 1500 of nerve identification and/or ablation, in accordance with many embodiments. It will be understood by those skilled in the art that the order of the steps may be switched, some of the steps may be combined, and/or some of the steps may be optional. The flowchart of FIG. 15 is one example of the method and is not intended to be limiting. Thus, it will be understood by those skilled in the art that various other operation(s) disclosed in this application may be used instead of those shown in FIG. 15. Method 1500 may be performed by any or all of the systems and components described above. For example, method 1500 may be performed by any of device 100, systems 300, 800, 1300, 1400, associated components thereof and/or any suitable combination thereof. The steps of method 1500 will now be described with reference to FIG. 15.

At step 1501, electrodes of a stimulator probe may be positioned at a desired location. For example, a distal end of a probe device such as device 100 may be inserted into a nasal cavity and positioned so that electrodes 104 are disposed adjacent to a region where a target nerve is expected to be located. The positioning may be done based on an anatomical landmark. In some embodiments, the positioning may further include expanding an end effector such as end effector 106 to place the electrodes in closer contact to the desired region.

Figure 16:
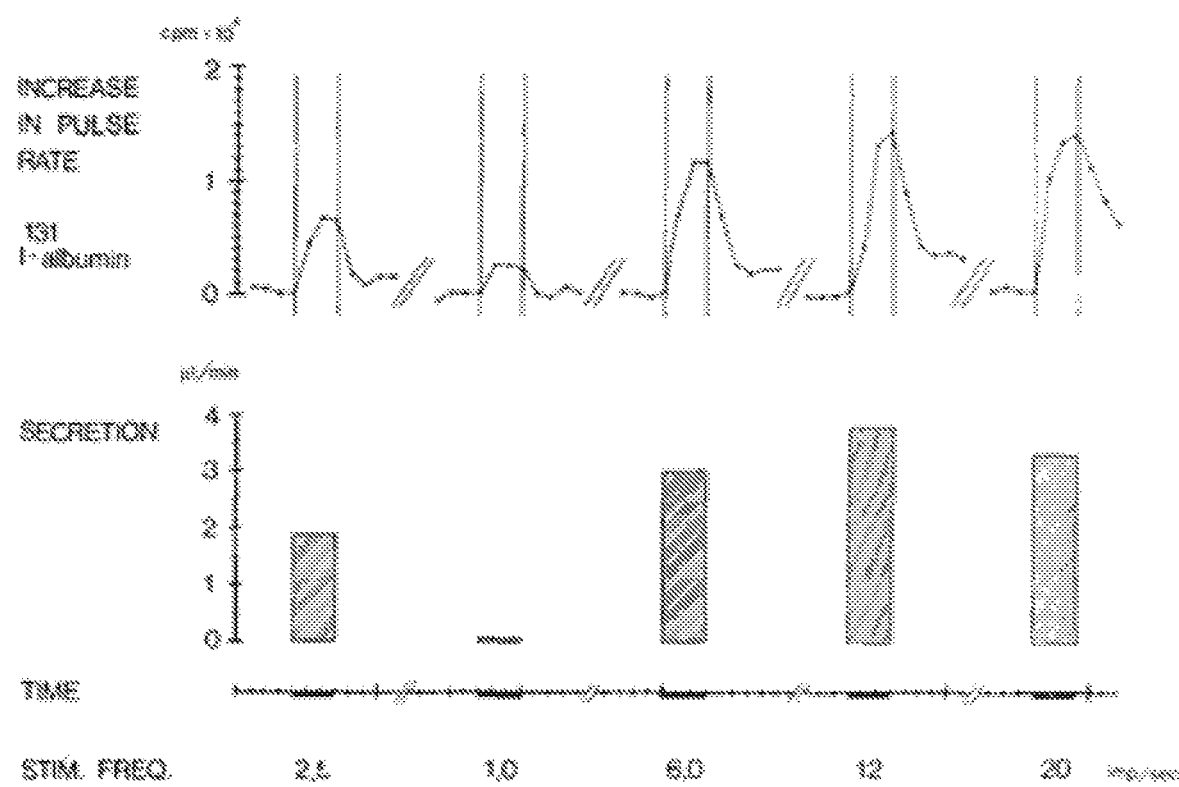
FIG. 16 shows experimental data illustrating the relationship between pulse rate and stimulation frequency and secretion and stimulation frequency.

Once the electrodes are positioned, at step 1502, a stimulus may be applied to the electrodes. In some embodiments, a pulsing stimulus may be applied to the electrodes by electrical source such as electrical source 304 described above with respect to systems 300 and/or 800. Any of the voltage, frequency, pulse rate, and current may be selected to obtain a particular response from the stimulation. For example, FIG. 16 shows experimental data illustrating the relationship between pulse rate and stimulation frequency and secretion. Accordingly, stimulation may be controlled using any of the prescribed parameters shown in FIG. 17, which shows some desirable electrical stimulation parameters in accordance with some embodiments. In some embodiments, the desired response may require delivering electric pulses through the electrodes at a frequency in a range from about 0.5 to about 12 impulses per second.

At step 1503, it is determined whether the desired response is obtained. As described above, this may be done by observation of the target tissue region and surrounding tissue for increased secretion and/or increased blood flow or other vascular response. For example, a desired result may be an increased secretion that indicates the electrodes are positioned near the targeted nerve. In some embodiments, the desired response may be determined based on a measured parameter including conductivity, resistivity, temperature, or other relevant parameter that may indicate increased secretion or vascular response. The desired response may be determined by a processor coupled to sensors disposed on the device as described above with respect to FIG. 13.

If it is determined that the desired response is not obtained, at step 1504, the electrode may be repositioned for further stimulation. For example, if no secretion or vascular response are observed in response to the stimulation, it may be determined that the electrodes are not near the targeted nerve, and they may be repositioned. As another example, if a threshold measurement is not sensed by relevant sensors described above, it may be determined that the electrodes are not adequately near the targeted nerve and they may be repositioned. Once repositioned, stimulus may be applied again as described with respect to step 1502 above.

If the desired response is obtained at step 1503, and an integrated ablation device is being used as determined at step 1505, then the targeted nerve may be ablated at step 1506. For example, if a device such as device 100 with both stimulating electrodes 104 and an ablation member 106 is being used, once the desired response is obtained at step 1503, the ablation member 106 may be used immediately to ablate the targeted nerve. In some embodiments, depending on the relative location of the electrodes and the ablation device, an optional step of adjusting the positioning of the ablation member may be needed after determining that the desired response is obtained. For example, if the electrodes are disposed distally of the ablation member (such as in system 800), the probe may be inserted further to align the ablation member with the identified target nerve for precise ablation.

If the desired response is obtained at step 1503, and an integrated ablation device is not being used as determined at step 1505, then the location may be marked at step 1507. For example, the coordinates of the identified target nerve may be stored as described above for use with an image guidance navigation system. Once the location is marked, it is determined whether additional target locations need to be identified at step 1508. If additional locations need to be identified, then the electrode may be repositioned as desired at step 1509. Once repositioned, stimulus may be applied again as described with respect to step 1502 above and the process may repeat as necessary until all locations are identified and/or marked.

If it is determined at step 1508 that no additional locations need to be identified, then the separate ablation member may be positioned for ablation at step 1510. Once positioned at a marked location, the ablation member may be used to ablate the target nerve at step 1506. If multiple target nerves or locations of a target nerve were marked, ablation member may be repositioned to each of the marked locations for ablation. It will be understood that image guided navigation may be employed as described above with respect to FIG. 14 in order to mark and recall the locations of target nerves.

Once ablation is performed at step 1510, the ablation may be confirmed at step 1511. For example, ablation may be confirmed by re-applying stimulus using the electrodes as described above with respect to step 1502, and observing or measuring the response thereto as described at step 1503. If no response (e.g. no increased secretion or vascular response in the region), or a response below a desired threshold is observed and/or measured, ablation may be complete and the process may end (or proceed to other target locations as described above). If a response such as increased secretion is observed and/or measured in response to the re-applied stimulus, the desired ablation may not be complete, and ablation may be repeated as described above with respect to step 1506 until ablation is confirmed. In some embodiments, it may be desirable to provide a waiting period after ablation at step 1506 and before re-applying stimulus to confirm ablation at step 1511. The waiting period may allow the region to recover so that an accurate evaluation of whether satisfactory ablation has been achieved can be obtained at step 1511.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims. For example, while symptoms of rhinitis and nasal nerves are described herein, it will be appreciated that any nerves which induce secretory or vascular changes in the tissue innervated by such nerves may be targeted, stimulated, identified, and/or ablated as described herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for ablating at least one nasal nerve associated with at least one symptom of rhinitis, the system comprising:
   a probe shaft having a proximal end and a distal end;
   an expandable ablation member permanently coupled to the distal end of the probe shaft;
   at least two electrodes disposed on a distal tip that is releasably coupled to the probe shaft, the at least two electrodes electrically coupled to an electrical source, wherein the at least two electrodes are configured to electrically stimulate at least one nasal nerve underlying a nasal surface in contact with the least two electrodes in response to an electrical current generated by the electrical source, wherein the least two electrodes are configured to detect a parameter indicative of a physiologic response to the electrical current; and
   a processor operatively coupled to the electrical source, wherein the processor is configured to:
      control the electrical current generated by the electrical source,
      receive the parameter indicative of the physiologic response to the electrical current, wherein the physiologic response is at least one physiologic response selected from a group consisting of: a change in nasal secretion and a change in arterial blood flow, and control, based on the parameter, the electrical current generated by the electrical source to cause the least two electrodes to ablate the at least one nasal nerve underlying the nasal surface to reduce the at least one symptom associated with rhinitis.

2. The system of claim 1, wherein the at least two electrodes are spaced apart in a range from 1 mm to 10 mm.

3. The system of claim 1, wherein the at least two electrodes are configured to stimulate 1 mm to 3 mm under the nasal surface in contact with the at least two electrodes.

4. The system of claim 1, wherein the probe shaft is sized so that the distal end of the probe shaft can reach a nasal mucosa covering a medial pterygoid plate of sphenoid bone through a passage of a middle nasal meatus from outside a nasal cavity.

5. The system of claim 1, wherein the processor is configured to control at least one feature selected from a group consisting of: a voltage, a frequency, and a pulse rate of the electrical current.

6. The system of claim 1, wherein the parameter is at least one parameter selected from a group consisting of: an electrical resistance, a temperature, and a degree of tumescence of the at least one nasal nerve underlying the nasal surface.

7. The system of claim 6, wherein the at least two electrodes are configured to detect a change in electrical resistance in an electrical signal passing through the at least two electrodes after stimulation of the at least one nasal nerve underlying the nasal surface, the change in resistance being indicative of a change in nasal secretion after stimulation of the at least one nasal nerve underlying the nasal surface.

8. The system of claim 1, wherein the expandable ablation member comprises an electrically non-conductive surface, and wherein the at least two electrodes are disposed on the electrically non-conductive surface of the expandable ablation member.

9. The system of claim 1, wherein a first electrode of the at least two electrodes is disposed at a central location of the expandable ablation member, and a second electrode of the at least two electrodes is disposed along a perimeter of the expandable ablation member.

10. The system of claim 1, wherein the at least two electrodes comprises four electrodes arranged rectangularly on the expandable ablation member such that the four electrodes are configured to stimulate four quadrants of the expandable ablation member.

11. The system of claim 1, wherein the expandable ablation member is configured to inflate so as to position the at least two electrodes adjacent to the nasal surface.

12. The system of claim 1, wherein the expandable ablation member comprises an expandable cryoablation member configured to cryogenically ablate the at least one nasal nerve to reduce at least one symptom associated with rhinitis.

13. The system of claim 1, wherein the distal tip includes a connector that is coupled to a connection portion of the probe shaft that is proximal to the expandable ablation member.

14. The system of claim 13, wherein the distal tip extends from the connection portion to a distal end disposed distally of the expandable ablation member, and wherein the at least two electrodes are disposed at the distal end of the distal tip such that the at least two electrodes are distal to the expandable ablation member.

15. The system of claim 1, wherein the processor is further configured to:

control the electrical current generated by the electrical source through the at least two electrodes after ablating the at least one nasal nerve to confirm that the at least one nasal nerve has been ablated.

16. The system of claim 1, further comprising:

at least one sensor, wherein the sensor is configured to detect the parameter indicative of a physiologic response to the electrical current, and wherein the at least one sensor is disposed on the probe shaft.

17. The system of claim 1, wherein controlling the electrical current generated by the electrical source comprises delivering electric pulses through the at least two electrodes at a frequency between 0.5 impulses per second to 12 impulses per second.

18. The system of claim 1, wherein the processor is further configured to:

measure a response to the electrical current using the at least two electrodes; and provide an indication to reposition the probe and stimulating the at least two electrodes until a desired response is measured using the at least two electrodes.

\* \* \* \* \*